US009176054B2

(12) United States Patent
Matsubara et al.

(10) Patent No.: US 9,176,054 B2
(45) Date of Patent: Nov. 3, 2015

(54) SYSTEM FOR TOMOGRAPHIC IMAGING USING COHERENT LIGHT THAT HAS A RANDOM PHASE DISTRIBUTION

(75) Inventors: Isao Matsubara, Tucson, AZ (US);
Chung-Chieh Yu, Tucson, AZ (US);
William Dallas, Tucson, AZ (US)

(73) Assignees: Canon Kabushiki Kaisha, Tokyo (JP);
THE ARIZONA BOARD OF REGENTS, Tucson, AZ (US)

( * ) Notice: Subject to any disclaimer, the term of this patent is extended or adjusted under 35 U.S.C. 154(b) by 0 days.

(21) Appl. No.: 13/491,322

(22) Filed: Jun. 7, 2012

(65) Prior Publication Data
US 2013/0329226 A1 Dec. 12, 2013

(51) Int. Cl.
*G01B 9/02* (2006.01)
*G01N 21/45* (2006.01)
*G01N 21/47* (2006.01)

(52) U.S. Cl.
CPC ............ *G01N 21/45* (2013.01); *G01B 9/02024* (2013.01); *G01N 21/4795* (2013.01); *G01B 2290/40* (2013.01)

(58) Field of Classification Search
CPC ........... G01N 2021/458; G01N 21/45–21/455; G01N 21/4795; G01B 9/0204; G01B 2290/40
USPC .......................... 356/457, 458, 496, 450, 456
See application file for complete search history.

(56) References Cited

U.S. PATENT DOCUMENTS

| 5,477,554 | A * | 12/1995 | Yoshii et al. | 372/9 |
| 7,324,209 | B2 * | 1/2008 | Hill | 356/495 |
| 7,463,366 | B2 * | 12/2008 | Dubois et al. | 356/520 |
| 2007/0014319 | A1 * | 1/2007 | Hill et al. | 372/20 |
| 2007/0121469 | A1 * | 5/2007 | Torii | 369/112.01 |
| 2008/0173789 | A1 * | 7/2008 | Minoda | 250/205 |
| 2010/0253986 | A1 * | 10/2010 | Awatsuji et al. | 359/10 |
| 2011/0002019 | A1 * | 1/2011 | Routley et al. | 359/9 |

(Continued)

FOREIGN PATENT DOCUMENTS

| JP | H11-014462 A | 1/1999 |
| JP | 2000-347105 A | 12/2000 |

(Continued)

OTHER PUBLICATIONS

YongKeun Park, Wonshik Choi, Zahid Yaqoob, Ramachandra Dasari, Kamran Badizadegan, Michael S. Feld, "Speckle-field digital holographic microscopy," Opt. Express 17, 12285-12292 (2009)).*

(Continued)

*Primary Examiner* — Michael A Lyons
*Assistant Examiner* — Violeta A Prieto
(74) *Attorney, Agent, or Firm* — Canon USA, Inc. I.P. Division

(57) ABSTRACT

The present invention provides an apparatus for tomographic imaging of an object. The apparatus includes a light unit configured to generate illumination, which comprises coherent light and has random phase distribution in a plane perpendicular to an optical axis, for illuminating an object, a coupler which combines a reference beam and an object beam for an interference, a shifter configured to shift relative phase difference between the object light and the reference coherent light, a detector configured to detect an interference caused by the reference coherent light and object light for the each phase, and a processor configured to calculate an optical propagation based on the detected interference for the each phase.

11 Claims, 25 Drawing Sheets

(56) References Cited

U.S. PATENT DOCUMENTS

| | | | |
|---|---|---|---|
| 2011/0292402 A1* | 12/2011 | Awatsuji et al. | 356/495 |
| 2012/0200901 A1* | 8/2012 | Dubois et al. | 359/15 |
| 2012/0289832 A1* | 11/2012 | Zhang et al. | 600/443 |
| 2013/0148182 A1* | 6/2013 | Yu et al. | 359/22 |

FOREIGN PATENT DOCUMENTS

| | | | |
|---|---|---|---|
| JP | 2004-538451 A | | 12/2004 |
| WO | WO 2011087802 A2 * | | 7/2011 |

OTHER PUBLICATIONS

Yasuhiro Awatsuji, Masaki Sasada, and Toshihiro Kubota, "Parallel quasi-phase-shifting digital holography," Applied Physics Letters 85, 1069 (2004)).*

Frank Dubois, Maria-Luisa Novella Requena, Christophe Minetti, Olivier Monnom, and Eric Istasse, "Partial spatial coherence effects in digital holographic microscopy with a laser source", vol. 43, No. 5, Applied Optics, 1131 (2004).*

Frank Dubois, Luc Joannes, and Jean-Claude Legros, "Improved three-dimensional imaging with a digital holography microscope with a source of partial spatial coherence", vol. 38, No. 34, Applied Optics, 7085 (1999).*

Christopher Fang-Yen et al., Video-rate tomographic phase microscopy, Journal of Biomedical Optics 16(1), 011005 (Jan. 2011), 1-5.

Arun Anand, Vani K. Chhaniwal, Giancarlo Pedrini, Wolfgang Osten, Digital holographic tomography of phase objects, Optical Measurement Systems for Industrial Inspection VI, Proceedings of SPIE, 2009, vol. 7389, Article 73890L, pp. 1-9, SPIE, Bellingham, WA 2009.

Tristan Colomb, Florian Dürr, Etienne Cuche, Pierre Marquet, Hans G. Limberger, René-Paul Salathé, and Christian Depeursinge, Polarization microscopy by use of digital holography: application to optical-fiber birefringence measurements, Applied Optics, Jul. 20, 2005, 44(21):4461-4469, Optical Society of America, Washington DC.

David S. Monaghan, Damien P. Kelly, Nitesh Pandey, Bryan M. Hennelly, Twin suppression in digital holography by means of speckle reduction, China-Ireland International Conference on Information and Communications Technologies, 2009, pp. 1-4.

* cited by examiner

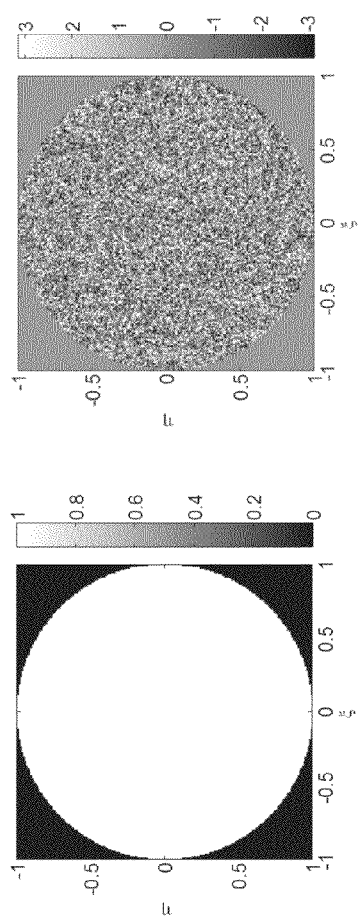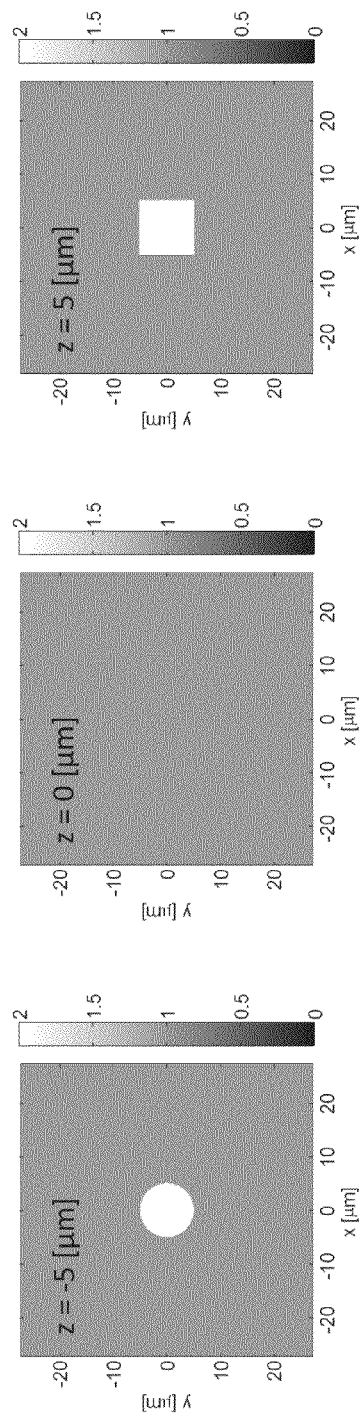

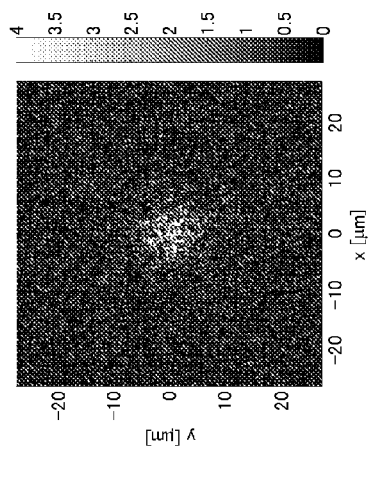
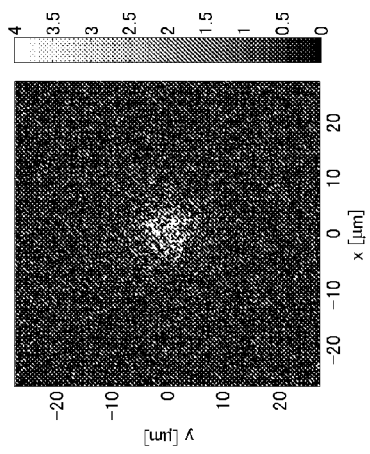
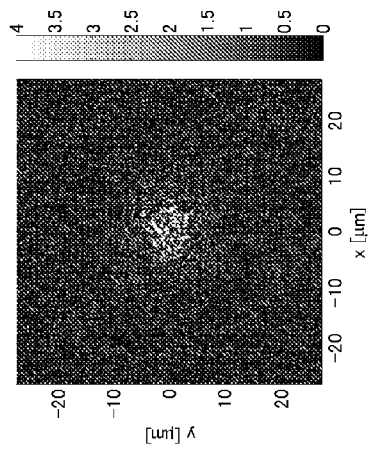
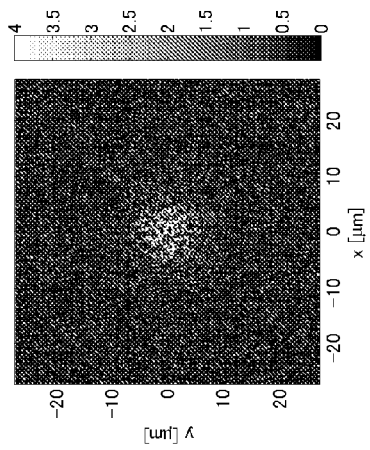
Fig. 6A
Fig. 6B
Fig. 6C
Fig. 6D

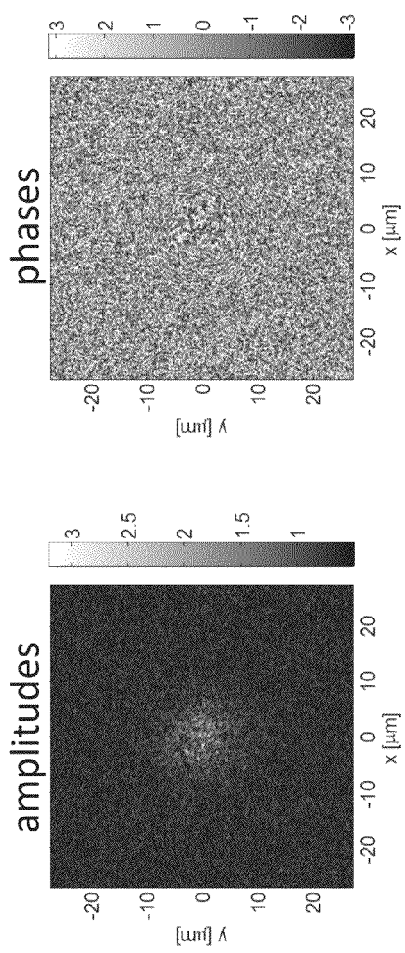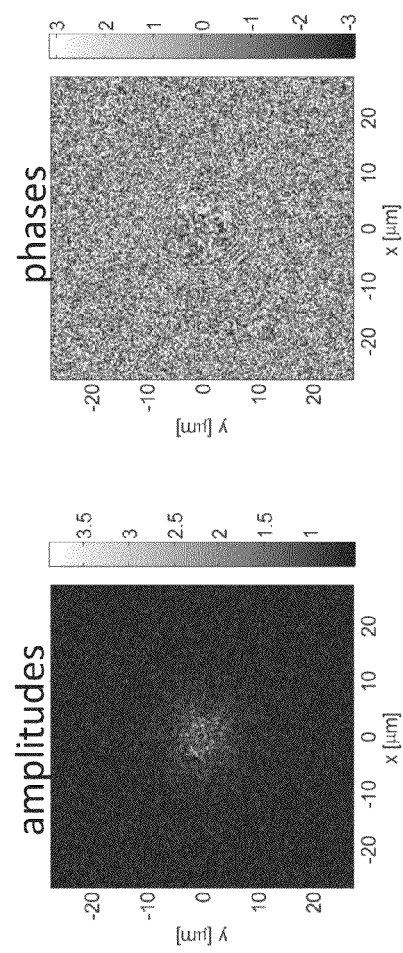
Fig. 7C
Fig. 7D

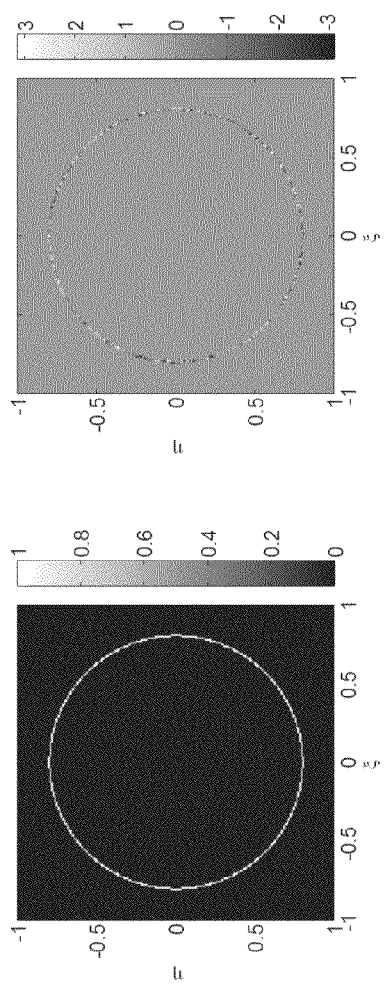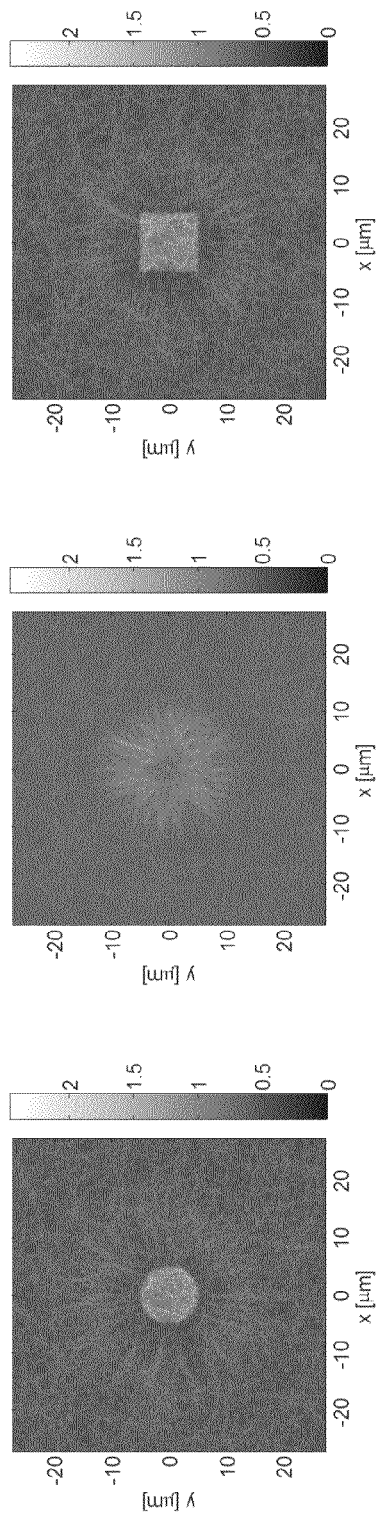

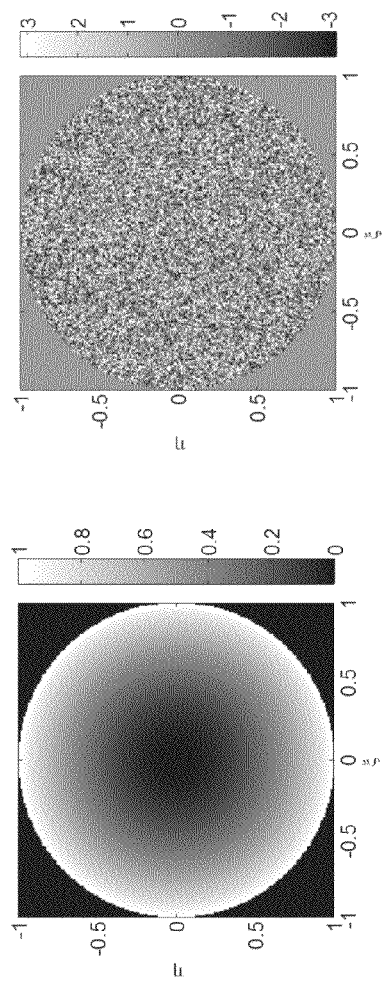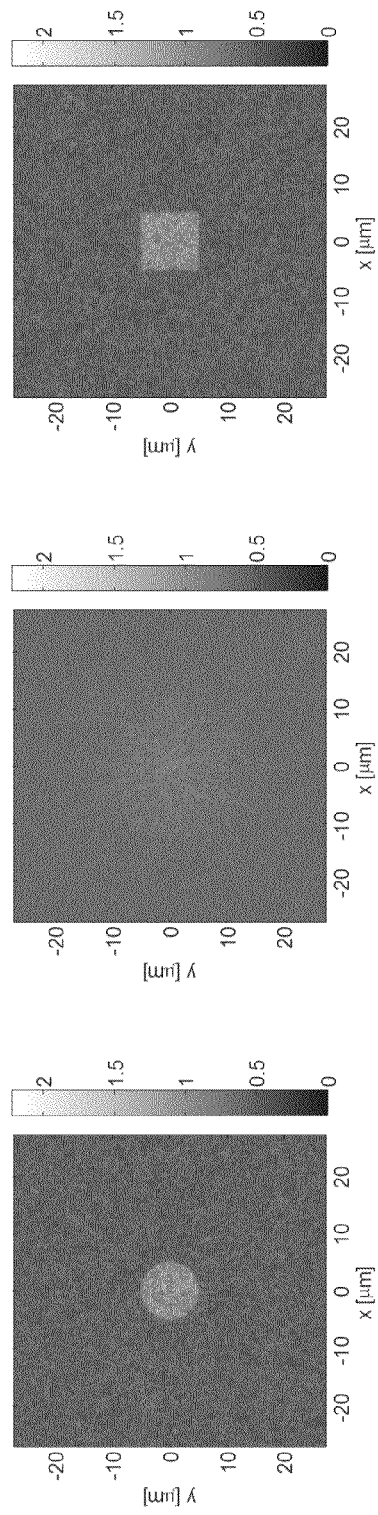

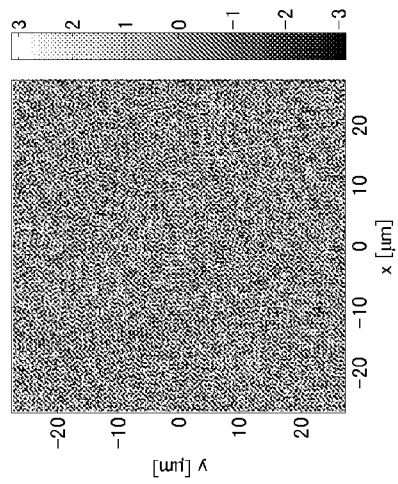
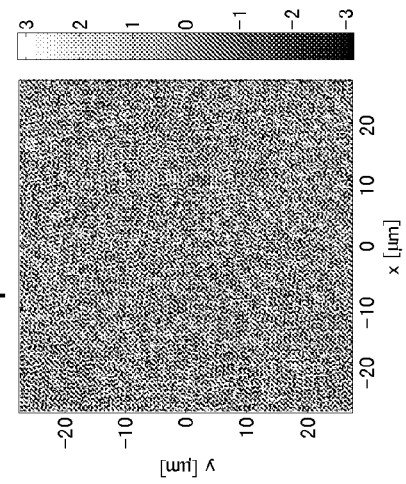
Fig. 20C
Fig. 20D
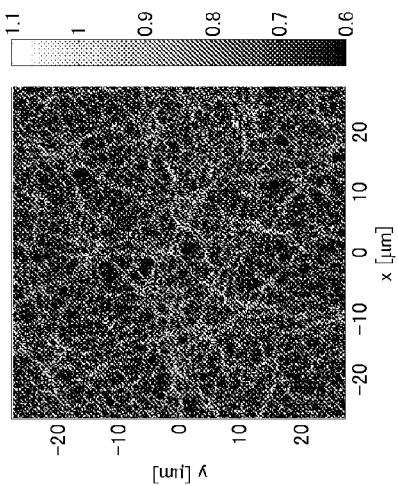
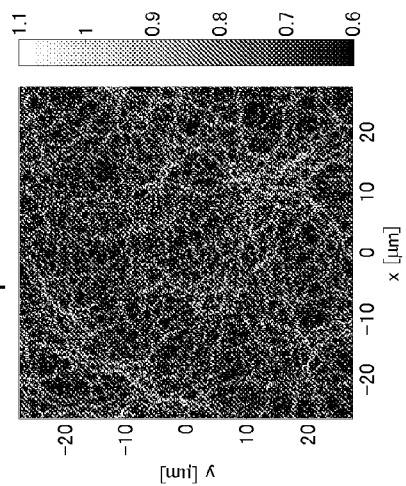

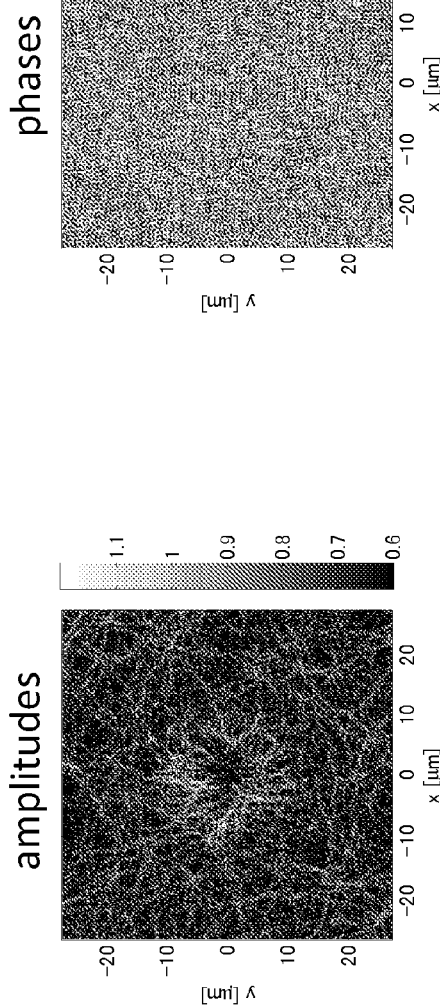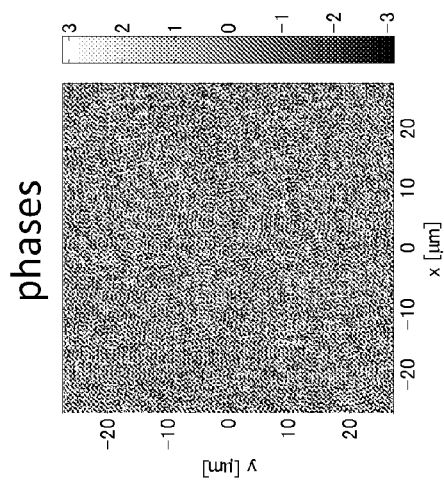
Fig. 21C
Fig. 21D

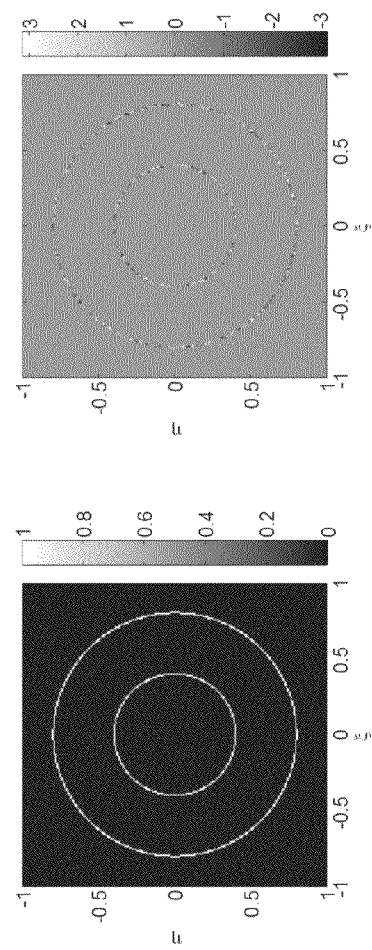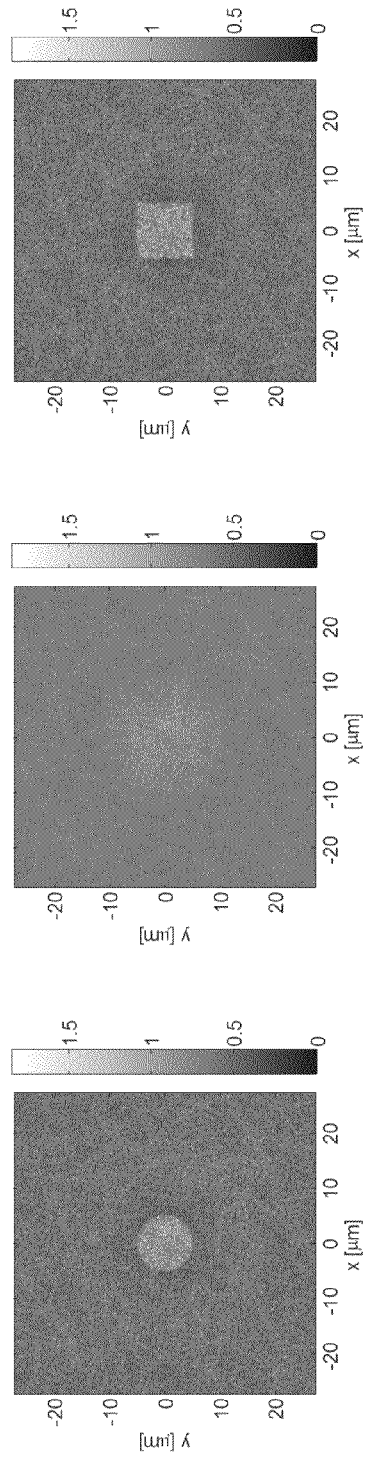

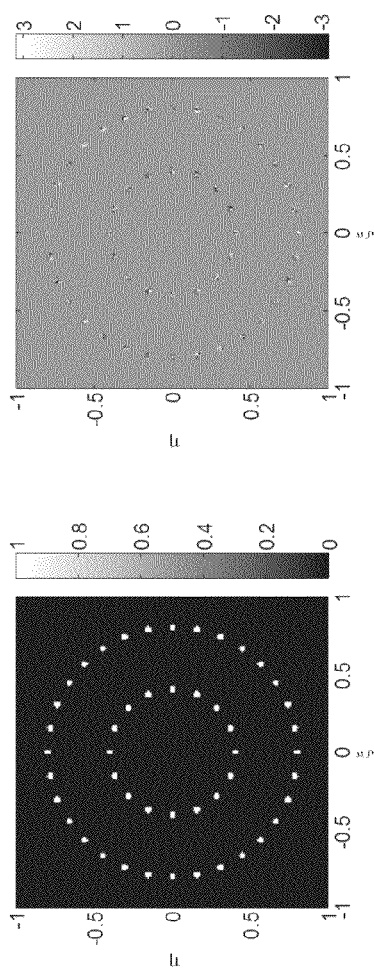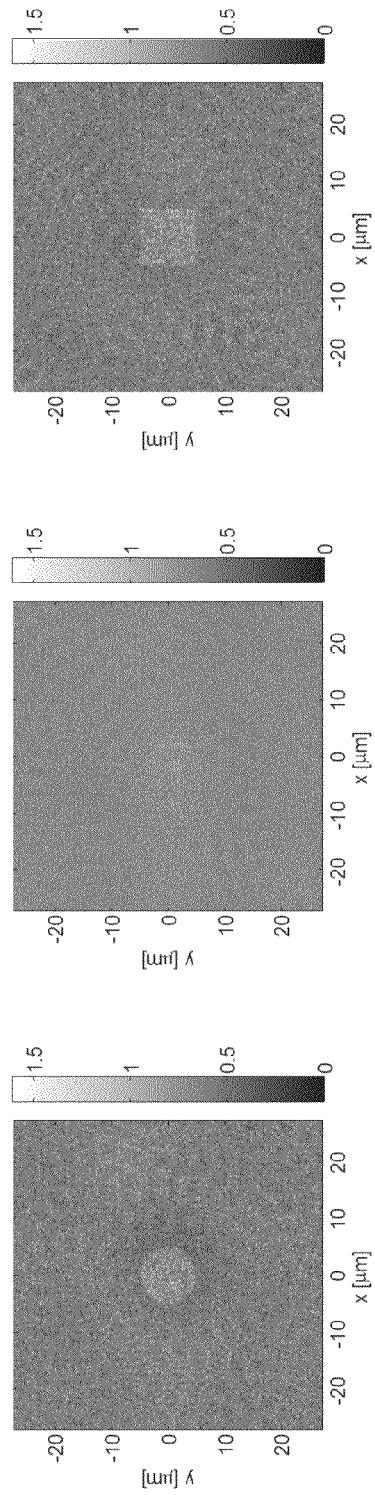

SYSTEM FOR TOMOGRAPHIC IMAGING USING COHERENT LIGHT THAT HAS A RANDOM PHASE DISTRIBUTION

BACKGROUND OF THE INVENTION

1. Field of the Invention

The present invention relates to an apparatus for tomographic imaging.

2. Description of the Related Art

In the field of the tomographic imaging, some techniques about tomographic measurement of 3-D images are conventionally known. For example, one technique is disclosed by Christopher Fang-Yen et al. Journal of Biomedical Optics 16(1), 011005 (January 2011), Title: Video-rate tomographic phase microscopy (hereinafter, "Fang-Yen"). More specifically, Fang-Yen discloses a technique to reconstruct 3-D images by using multi angle scanning. According to this technique, many illumination angles, e.g. 100, which means 100 shots, are required, because 3-D images are reconstructed from projected images (according to complex amplitudes calculated based holograms). Therefore, reasonable images can't be expected with several shots, e.g. 4 shots. Moreover 3-D images can't be reconstructed with one shot. Therefore, according to prior art (e.g., Fang-Yen), many shots, and therefore a long time, is required for reconstructing the 3-D image.

SUMMARY OF THE INVENTION

According to an embodiment of the present invention, there is provided an apparatus for tomographic imaging of an object which includes, a light unit configured to generate illumination, which comprises coherent light and has random phase distribution in a plane perpendicular to an optical axis, to an object, a coupler which combines a reference coherent light and an object light which is from the light unit and passed through the object, the reference coherent light and the object light being interfered, a shifter configured to shift relative phase difference between the object light and the reference coherent light, a detector configured to detect an interference caused by the reference coherent light and object light for the each phase; and, a processor configured to calculate an optical propagation based on the detected interference for the each phase. Accordingly, taking 3-D images may be performed in less time.

Further features of the present invention will become apparent from the following description of exemplary embodiments with reference to the attached drawings.

BRIEF DESCRIPTION OF THE DRAWINGS

FIG. 3A illustrates an exemplary illumination amplitude distribution with a disk shape FIG. 3B illustrates an exemplary illumination phase distribution with a disk shape.

FIGS. 4A-C are amplitude distributions at z=−5 to +5 [μm] illustrating an example of test object.

FIGS. 6A-6D illustrate exemplary phase shift holograms with π/2 phase shift, with π phase shift, with 3π/2 phase shift and with 2π phase shift.

FIGS. 7A-7D illustrate exemplary complex amplitudes.

FIG. 10A illustrates another exemplary illumination amplitude distribution with an annular shape.

FIG. 10B illustrates another exemplary illumination phase distribution with the annular shape.

FIGS. 11A-11C illustrate another exemplary reconstructed images at z=−5 to +5 [μm] with the annular shape illumination.

FIG. 12A illustrates another exemplary illumination amplitude distribution with a bowl shape.

FIG. 12B illustrates another exemplary illumination phase distribution with the bowl shape.

FIGS. 13A-13C illustrate another exemplary reconstructed images at z=−5 to +5 [μm] with the bowl shape illumination.

FIGS. 20A-D illustrate exemplary complex amplitudes according to an exemplary embodiment.

FIGS. 21A-21D illustrate exemplary recalculated complex amplitudes according to an exemplary embodiment.

FIG. 22A illustrates another exemplary illumination amplitude distribution with a double annular shape.

FIG. 22B illustrates another exemplary illumination phase distribution with the double annular shape.

FIGS. 23A-23C illustrate another exemplary reconstructed images at z=−5 to +5 [μm] with the double annular shape illumination.

FIG. 24A illustrates another exemplary illumination amplitude distribution with a double annular dot shape.

FIG. 24B illustrates another exemplary illumination phase distribution with the double annular dot shape.

FIGS. 25A-C illustrate another exemplary reconstructed images at z=−5 to +5 [μm] with the double annular dot shape illumination.

DESCRIPTION OF THE EMBODIMENTS

Figure 1A:
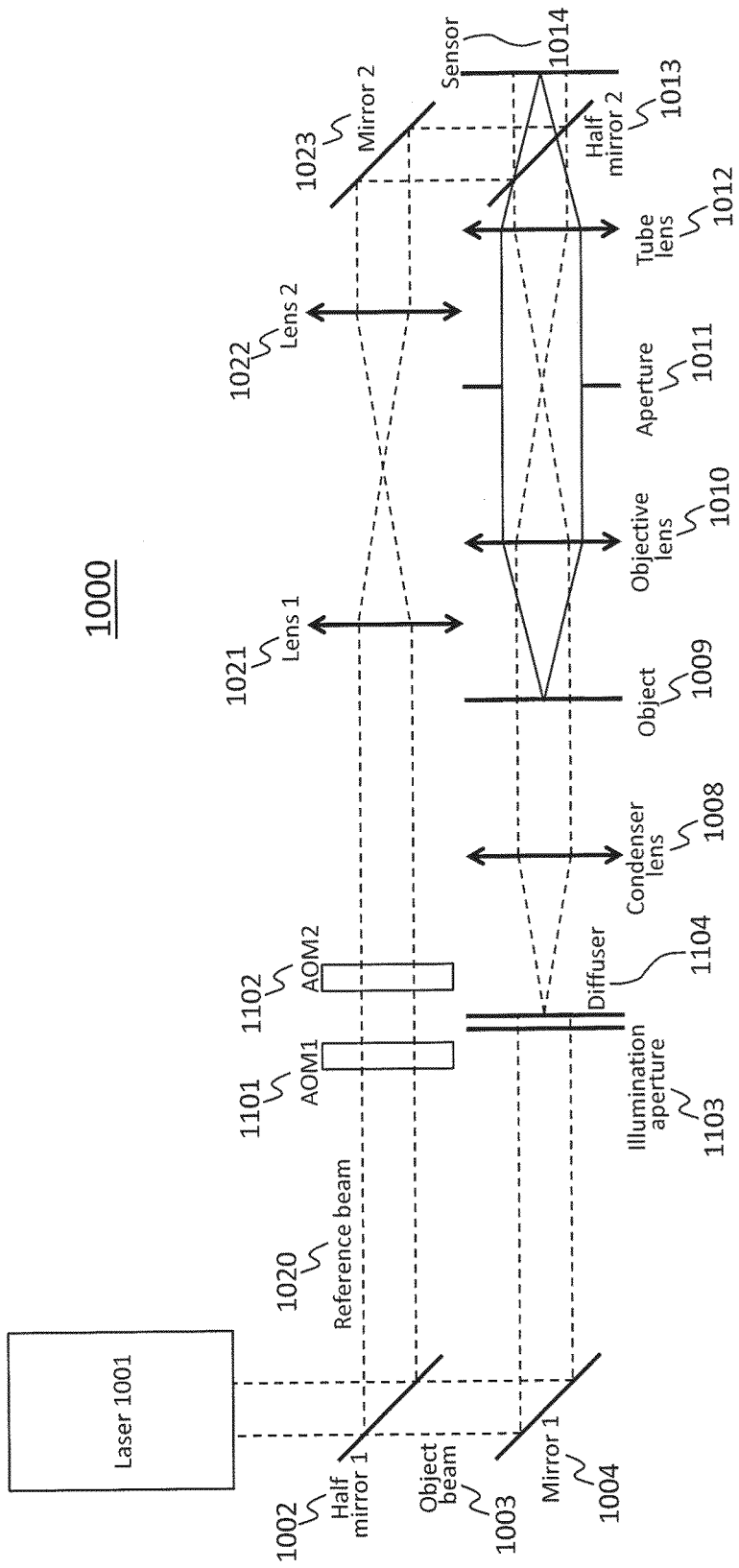
FIGS. 1A-1C illustrate exemplary system configurations to take phase shift holograms (complex amplitudes).

Exemplary embodiments according to the present invention will be described below with reference to the attached drawings. The same reference numerals denote the same members throughout the drawings, and a repetitive description thereof will not be given.

[Measurement of Amplitude Object]

FIG. 1A illustrates one example of an optical system/apparatus 1000 for tomographic imaging of an object. The system in the exemplary embodiment can support both an amplitude object and a phase object by replacing an illumination distribution (illumination aperture 1103) and an aperture 1011. FIG. 1A illustrates the system when it supports the amplitude object and is described next. Details of the system for the phase object will be described later. As shown in FIG. 1A, a coherent light beam is generated by a laser source (laser 1001), and the beam is separated by a half mirror 1002 into an object beam 1003 and a reference beam 1020.

The object beam is reflected by a mirror1 1004, and goes through an illumination aperture 1103 and a diffuser 1104. The Laser 1001, the mirror1 1004, the illumination aperture 1103, and the diffuser 1104 work as a light unit.

A motor (not shown) drives the diffuser 1104, and the diffuser 1104 rotates around an optical axis in accordance with the motor's driving. A CPU 2001 (shown in FIG. 2) outputs control signals to the motor via an I/O controller 2006 and controls a rotating position of the diffuser 1104, the rotating position corresponding to an angle of rotation. The CPU 2001 may change the rotating position to change the random phase distribution of coherent light which irradiates an object 1009, the random distribution being in a plane perpendicular to the optical axis. However the present exemplary embodiment is not limited to the changing method for the random phase distribution. For example, it can also be applied to move diffuser to any direction (e.g. left, right, up or down) in accordance with the motor's driving. In this way, the same effect can also be acquired by using various method of rotating position.

Then, the beam goes through a condenser lens 1008 which is located at the focal length away from the diffuser 1104 and goes through the object 1009. The beam is interfered by the object. Then, the beam goes through an objective lens 1010, an aperture 1011, and a tube lens 1012. The object beam is integrated by a half mirror2 1013 with the reference beam, and these beams (the reference beam 1020 and the object beam 1003) are interfered. The integrated beam (interference) is detected by a sensor 1014. A mirror2 1023 and half mirror2 1013 work as a coupler.

After the reference beam is generated by the half mirror1 1002, the reference beam 1020 goes through two Acousto-optic modulators (AOMs) 1101 and 1102, which make a plurality of phase shifts of the reference beam. An AOM behaves like grating, so the combination of two AOMs can generate a phase delay (phase shift) by changing an optical path length along the optical axis. AOMs 1101 and 1102 work as a shifter that shift relative phase difference between the object light and the reference beam 1020 (reference coherent light). Then, the reference beam 1020 goes through lens1 1021 and lens2 1022, which are for changing the reference beam diameters to match the object beam diameter. Then, reference beam 1020 is reflected by a mirror2 1023. Then, the reference beam 1020, which has been set to one of plurality of phase shifts by the AOMs, is integrated by the half mirror2 1013 with the object beam as described above. The sensor 1014 includes photo-detectors. The photo-detectors are arranged in a two-dimensional array. Each photo-detector receives light and outputs an electrical signal based on a light amount of received light. An example of sensor 1014 is a CMOS sensor.

Figure 1B:
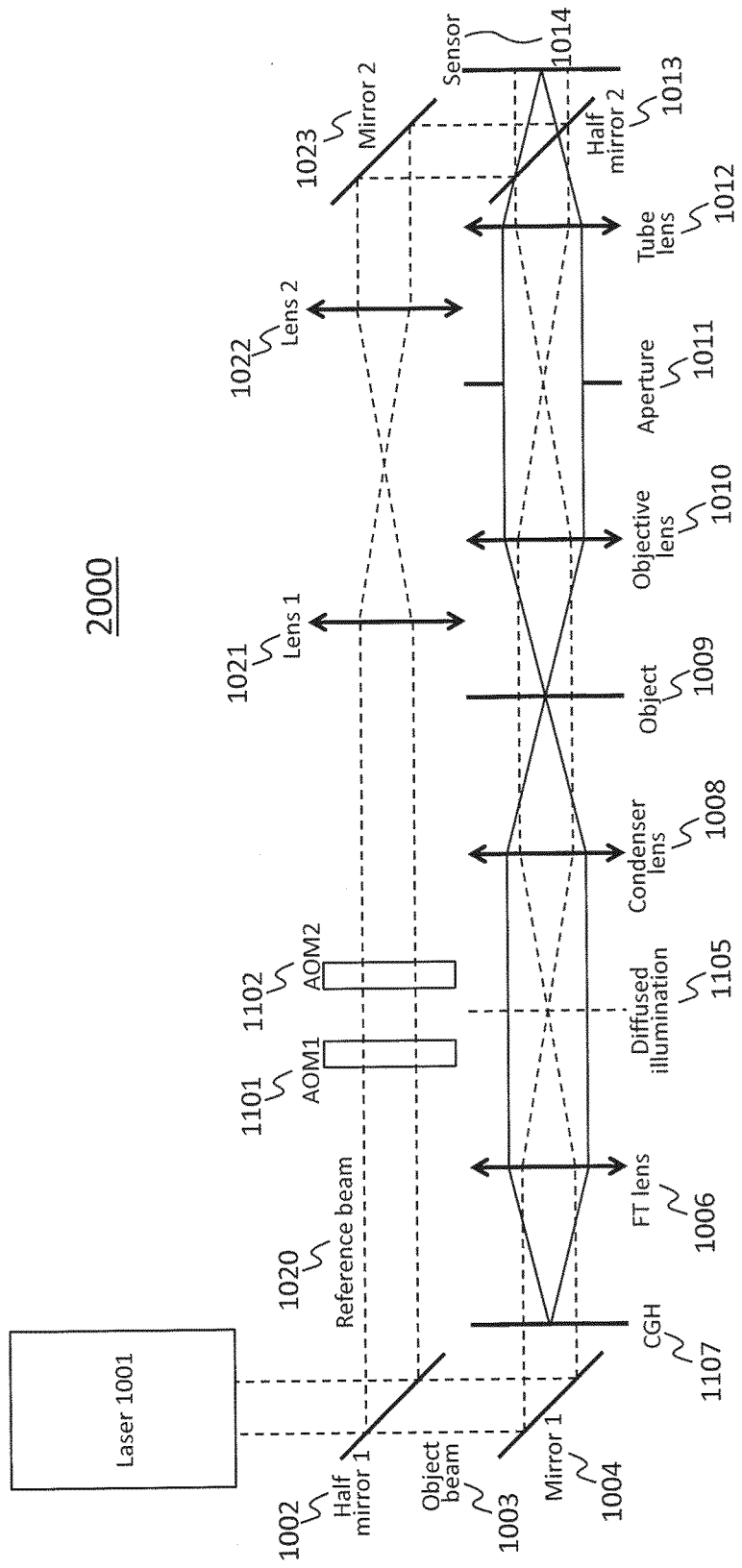

FIG. 1B shows another example of the optical system. The optical system 2000 includes a computer generated hologram (CGH) 1107 instead of an illumination aperture 1103 and a diffuser 1104 in the optical system 1000. A diffused illumination 1105 is generated by the CGH 1107 and FT lens 1006. The Laser 1001, the mirror1 1004, and the CGH 1107 work as a light unit. Other parts are similar to those illustrated in FIG. 1A and described above, and therefore, a description thereof is not repeated. Different points will be mainly described hereinafter. The CGH 1107 is designed for having a desired illumination distribution at the plane which is called a diffused illumination 1105. The CGH plate 1107 can be rotated. When the CGH plate 1107 is rotated, the random phase distribution of coherent light is also changed in accordance with the CGH plate's position.

Figure 1C:
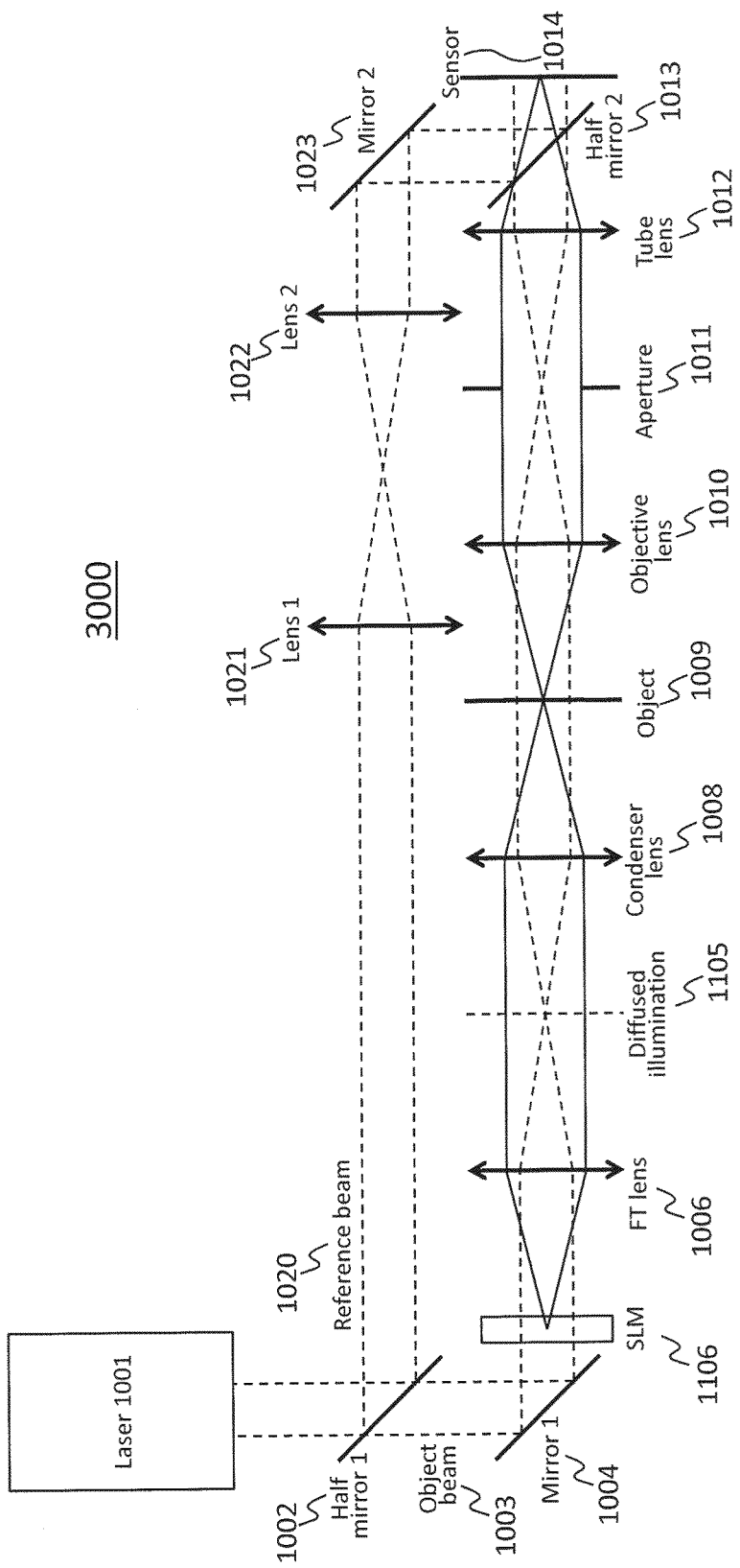

FIG. 1C shows another example of the optical system. The optical system 3000 includes a spatial light modulator (SLM) 1106. The Laser 1001, the mirror1 1004, and the SLM 1106 work as a light unit. The SLM also work as a phase shifter. The SLM 1106 can shift the phase at each pixel separately, and when it shifts the same phase at all pixels, it can work the phase shifter which shifts relative phase difference between the object light and the reference beam 1020 (reference coherent light). Other parts are similar to those illustrated in FIG. 1A or FIG. 1B and described above, and therefore, a description thereof is not repeated. Different points will be mainly described hereinafter. By making the SLM 1106 have the same distribution for the CGH, the diffused illumination 1105 can be generated. Note that, the SLM has a function for phase shifting, so AOMs 1101 and 1102 may not be required for the system 3000.

Figure 2:
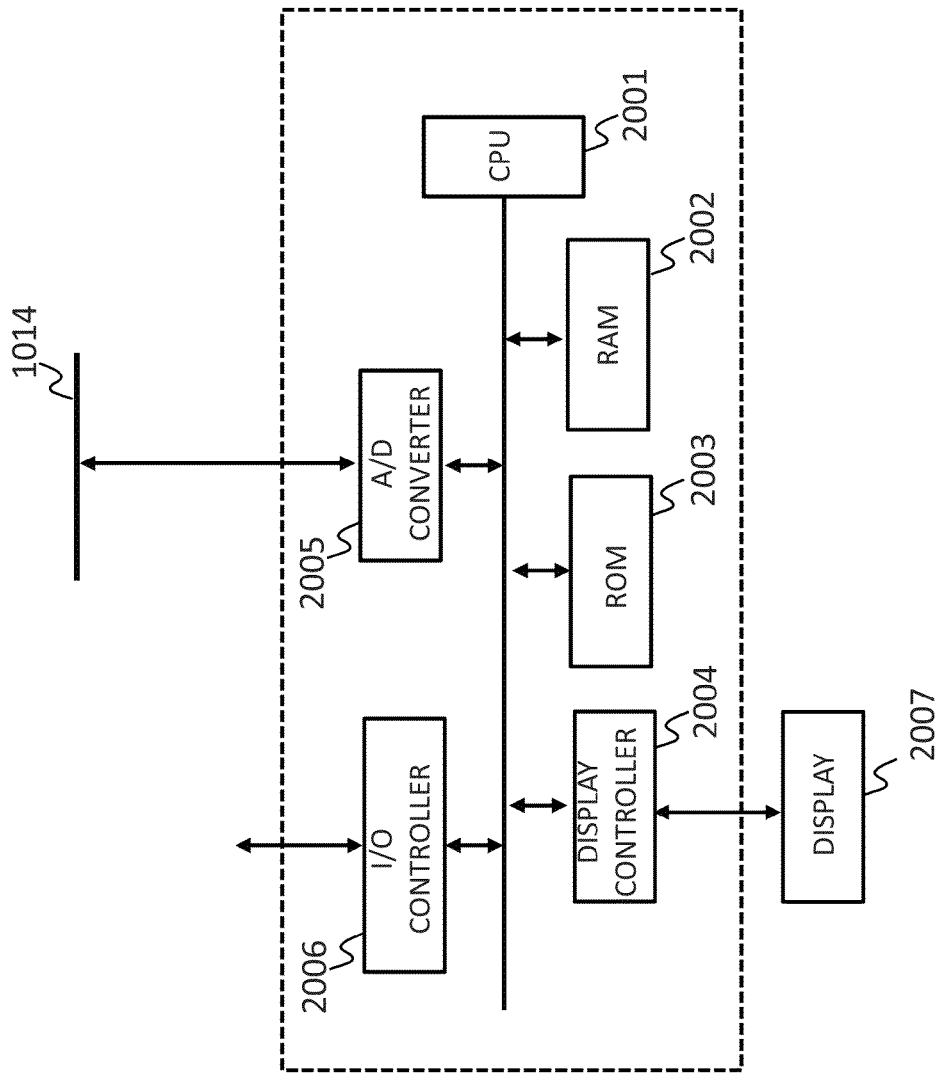
FIG. 2 is a block diagram illustrating an example of computer hardware.

FIG. 2 illustrates an exemplary hardware configuration of the data processing apparatuses. The CPU 2001 controls each element in accordance with a variety of programs stored in a read-only memory (ROM) 2003 using a random access memory (RAM) 2002 as a main memory and a work area. The display controller 2004 controls a display 2007. The A/D converter 2005 converts analog signals into digital signals. The signals detected by the sensor 1014 are input into A/D converter 2005 and then A/D converter 2005 converts the input signals. I/O controller 2006 is an interface for communication with an external device. I/O controller 2006 is connected to a motor or driving source. For example, I/O controller 2006 may be connected to the motor that drives the rotating position of the diffuser 1104. Also, the CPU 2001 outputs a control signal for setting phase of the AOM1 1101 and AOM2 1102 or phase of the SLM 1106.

FIGS. 3A and 3B shows one example of the illumination distribution with a disk shape. FIG. 3A shows amplitude distribution and FIG. 3B shows phase distribution. The illumination plane, which is defined by the illumination aperture 1103 and the diffuser 1104 of FIG. 1A, is conjugate with the aperture plane, which is defined by the aperture 1011. This shape has an ability to make image of each point in the object 1009 sparse in defocused plane which is forward or back side of the sensor 1014 and which is perpendicular to the optical axis. As shown in FIG. 3B, the diffuser 1104 causes the phase distribution to become random.

FIGS. 4A, 4B and 4C show the amplitude distributions at (a) z=−5 [μm], (b) z=0 [μm], (c) z=5 [μm], respectively, of the test object (object 1109). The axis z is along the optical axis. This test object can be thought of as a fluorescent object. For example, there is a disk shape fluorescent object at z=−5 [μm], and there is a rectangle shape fluorescent object at z=5 [μm]. A remarkable thing is that there is nothing at z=0 [μm], so the nothing, means no shape of the disk or the rectangle, is expected as a reconstructed image there.

<Flowchart for Calculating Complex Amplitudes and Numerical Focusing>

Figure 5:
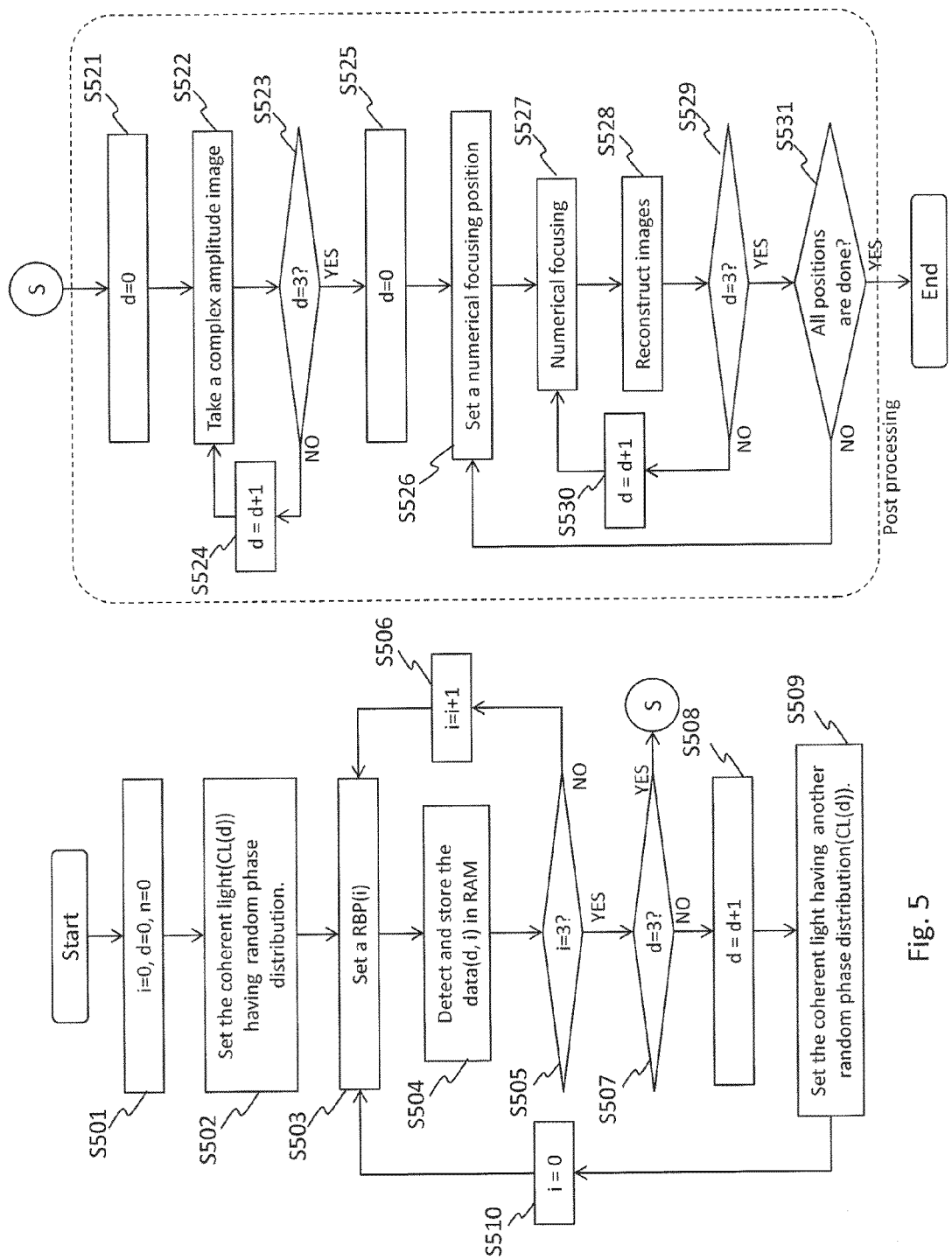
FIG. 5 is a flow chart illustrating taking tomographic images according to an exemplary embodiment.

FIG. 5 shows a flowchart for calculating complex amplitudes and numerical focusing. In step S501, the CPU 2001 initializes variables "i", "d" and "n" to zero. In step S502, the CPU 2001 sets CL(d). "CL" stands for coherent light having static random phase distribution. For example, the CPU 2001 sets the diffuser for the 1st position. Note that, several ways to set the diffuser will be explained later; one of those is rotating the diffuser.

In step S503, the CPU 2001 sets RBP (i). "RBP" stands for reference beam phase. In step S504, sensor 1014 detects integrated beam. When the signal corresponding to detected beam is input to A/D converter 2005, the A/D converter 2005 converts the input analog signal into a digital signal. Then the CPU 2001 stores the converted digital data as data (d, i) in the RAM 2002 temporarily. Data(d, i) means a set of digital signals according to detection results by the sensor 1014 when the CPU 2001 sets CL(d) as a phase distribution and RBP(i) as a reference beam phase, with each of the digital signals corresponding to each (x, y) coordinate. In brief, the data(d, i) is data which has a two-dimensional distribution. FIGS. 6A-D illustrate the data(d, i). Also, each of the digital signals indicates intensity of detected light, each intensity corresponds to "Ii" in equation (1) explained later in detail.

In step S505, the CPU 2001 determines if variable "i" equals 3 or not. If variable "i" doesn't equal 3, the CPU 2001 adds 1 to variable "i" in step S506 and the process returns to step S503, then the CPU 2001 changes the reference beam which was previously set in step S503. On the other hand, if variable "i" equals 3 then the process proceeds to step S507. In step S507, the CPU 2001 determines if variable "d" equals 3. If variable "d" doesn't equal 3 then CPU 2001 proceeds to step S508. In step S508, the CPU 2001 adds 1 to variable "d". In step S509, CPU 2001 sets CL(d), i.e., coherent light having another random phase distribution is set. Specifically, for example, the CPU 2001 controls a motor (not shown) to rotate 90 degrees (H/2) the diffuser 1104 via the I/O controller 2006. Then the phase distribution of the illumination, which irradiates the object 1009, changes. Also, after-rotating position can be called 2nd position against the 1st position. The 1st position corresponds to first random phase distribution and the 2nd position corresponds to second random phase distribution. If "d" doesn't equal 3, the CPU 2001 initializes variables "i" to zero in step S510. Then the CPU 2001 returns processing to step S503. On the other hand, if variable "d" equals 3, the CPU 2001 proceeds to step S521.

In step S521, the CPU 2001 initializes variables "d" to zero. Next, in step S522, the CPU 2001 takes complex amplitude image (calculates complex amplitude). More specifically, the CPU 2001 reads the data corresponding to current value of variable "d" and stored in the RAM 2002. For example, when variables "d" is "0", the CPU 2001 reads data(0, 0), data(0, 1), data(0, 2), data(0, 3) from the RAM 2002. These data can be considered as FIGS. 6A-6D. Then the CPU 2001 calculates complex amplitudes by using read data and formula (1). Details for formula (1) will be described later. More details regarding FIGS. 6A-6D will also be described later. In step S523, the CPU 2001 determines if variable "d" is equal to 3 or not. If "d" doesn't equal 3 then the CPU 2001 adds 1 to variable "d" in step S524, then the CPU 2001 returns processing to step S522. On the other hand, if variable "d" is equal to 3, the CPU 2001 proceeds processing to step S525 and initializes variable "d" to zero. In step S526 the CPU 2001 determines a numerical focusing position. For example, as the positions, z=−5 [μm], z=0 [μm], z=+5 [μm]. In step S526, the CPU 2001 sets target numerical focusing position. Then, the CPU 2001 calculates numerical focusing in step S527 and re-constructs images in step S528. In steps S529 and S530, the CPU 2001 processes the same as those of step S523 and S524, respectively, (i.e., determines if "d" is equal to 3, and if not, increments d by 1). In step S531, the CPU 2001 determines if all positions are done or not. If it is determined that all positions are not done, the CPU 2001 returns processing to step S526. On the other hand, if it is determined that all positions are done, the CPU 2001 ends processing of this flow chart. After processing, calculation results can be displayed on the display.

Although it's described that the CPU 2001 calculates the complex amplitude and the numerical focusing after all detected data(d, i) are stored in the RAM 2002, the exemplary embodiment isn't limited to this. For example, when the CPU 2001 stores the data(d, i) for a certain "d" value and all "i", values (e.g., d=0; i=1, 2, 3) the CPU 2001 may calculate complex amplitude and numerical focusing for the certain "d" value and the all "i" values before the CPU 2001 sets the next "d" value (e.g., d=1; i=1, 2, 3) in the sequence into CL(d).

The complex amplitude as E-field can't be detected directly. As one way to obtain the complex amplitude, there is a phase shift method described above. FIGS. 6A, 6B, 6C and 6D show phase shift holograms with four phase shifted reference beams, π/2, π, 3π/2 and 2π, respectively. Let phase shift holograms be I0, I1, I2 and I3. "I0" corresponds to one white dot in FIGS. 6A-6D, the white dot being detected by any one of the photo detector. Detection results detected by each photo-detector are shown as set of dots in FIGS. 6A-6D. Also I0 through I3 are detected by same photo detector. Then, the complex amplitude "v" can be calculated with the following equation (1) by the CPU 2001. This equation (1) is one example to calculate "v" under the condition that the intensities of the object beam and the reference beam are the same or similar. Also the CPU 2001 calculates all complex amplitudes according to each of photo-detectors. These processes correspond to step of S522 in FIG. 5.

$$v(x, y, 0) = \sqrt{\frac{I0 + I1 + I2 + I3}{4}} \exp\left[i \cdot \arctan\left(\frac{I1 - I3}{I0 - I2}\right)\right] \quad (1)$$

Here, √((I0+I1+I2+I3)/4) of equation (1) corresponds to amplitude in FIGS. 7A-7D, and arctan((I1−I3)/(I0−I2)) of equation (1) corresponds to phase in FIGS. 7A-7D. The CPU 2001 inputs v(x, y, 0) which is left side of equation (1) into v(x, y, 0) which is in right side of equation (1).

FIGS. 7A-7D show exemplary complex amplitudes calculated by the CPU 2001 based on the equation (1). For example, FIG. 7A can be corresponded to "d=0", FIG. 7B can be corresponded to "d=1", FIG. 7C can be corresponded to "d=2", and FIG. 7D can be corresponded to "d=3". These planes conjugate with z=0 [μm] of the object plane. Although the amplitudes in FIGS. 7A, 7B, 7C and 7D include the shape of the objects at z=±5 [μm], it may be difficult to find the shape with the naked eye. The phases in FIGS. 7A, 7B, 7C and 7D may look random but have some information for calculating reconstructed images of the objects at z=±5 [μm].

Figure 7A:
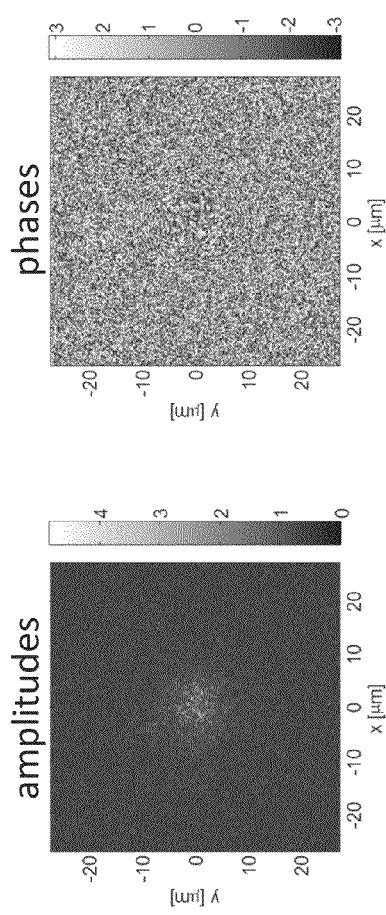
Figure 7B:
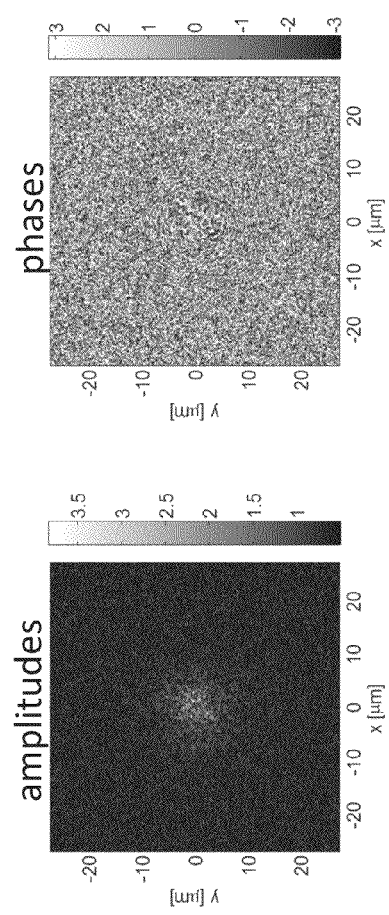
Figure 9A:
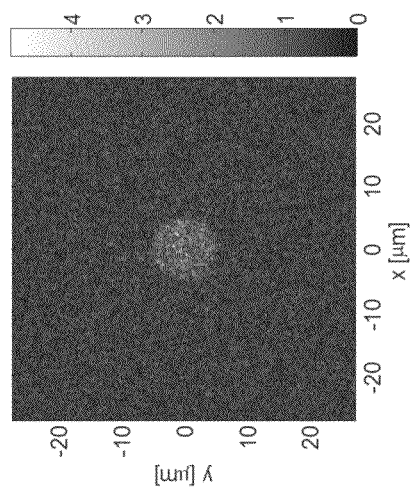
FIGS. 9A-9C illustrate another exemplary reconstructed images at z=−5 to +5 [μm] with the disk shape illumination.
Figure 9B:
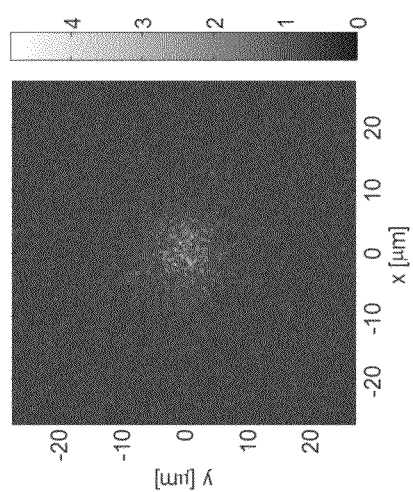
Figure 9C:
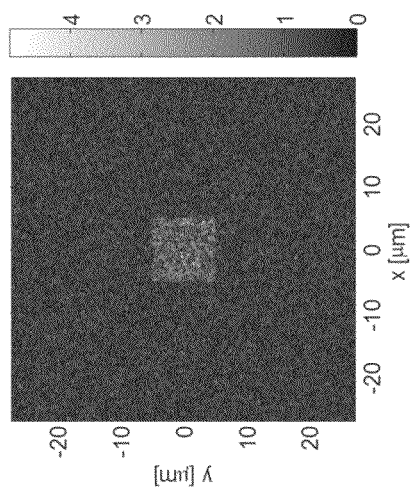

Here, the numerical focusing is explained in detail. The explanation also corresponds to detailed explanation of step S527. The numerical focusing is a calculation method for an optical propagation of the electric field (complex amplitude). The following equations show one example for the calculation, which propagates the electric field v(x, y) from z=−k [μm] to z=+k [μm]. This method is referred to as the propagation of the angular spectrum. v(x, y, 0) means the electric field at z=0, and FIG. 7A can be thought as v(x, y, 0). Equation (2) is a Fourier transform, so V(α, β, 0) is a spectrum of v(x, y, z(μm)). Equation (3) is an inverse Fourier transform after applying the phase factor for the propagation, exp[i*2π/λ*sqrt(1−α^2−β^2)]. Then, v(x, y, z) is the electric field at z=k as a result. FIG. 9A shows the amplitude of v(x, y, −5) calculated based on the FIG. 7A, and FIG. 9B shows the amplitude of v(x, y, 0), and FIG. 9C shows the amplitude of v(x, y, 5).

Where (x, y, z) is a location in the real space, and (α, β) is a location in Fourier space, and λ is a wavelength.

$$V\left(\frac{\alpha}{\lambda}, \frac{\beta}{\lambda}, 0\right) = \int\int v(x, y, 0)\exp\left[-i2\pi\left(\frac{\alpha}{\lambda}x + \frac{\beta}{\lambda}y\right)\right]dxdy \quad (2)$$

$$v(x, y, z) = \int\int V\left(\frac{\alpha}{\lambda}, \frac{\beta}{\lambda}, 0\right)\exp\left[i\frac{2\pi}{\lambda}\sqrt{1-\alpha^2-\beta^2}\,z\right] \quad (3)$$
$$circ\left(\sqrt{\alpha^2+\beta^2}\right)\exp\left[i2\pi\left(\frac{\alpha}{\lambda}x + \frac{\beta}{\lambda}y\right)\right]d\frac{\alpha}{\lambda}d\frac{\beta}{\lambda}$$

Figure 8C:
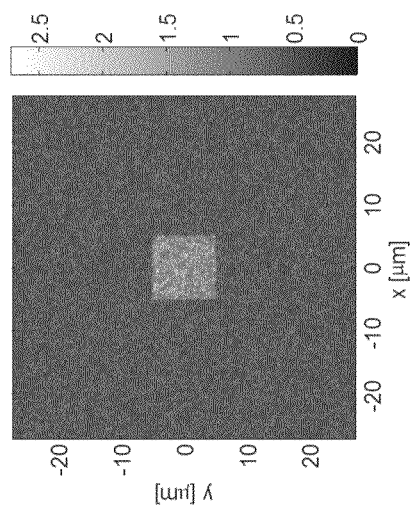
FIGS. 8A-8C illustrate exemplary reconstructed images at z=−5 to +5 [μm] with the disk shape illumination.
Figure 8B:
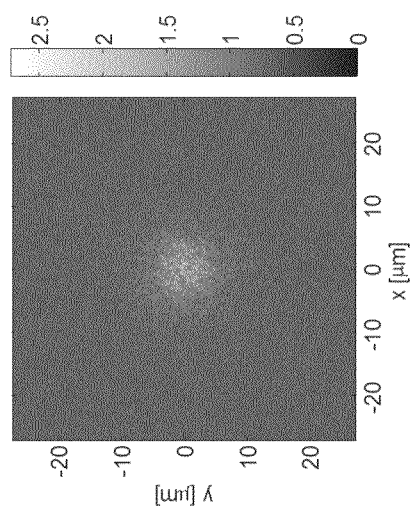
Figure 8A:
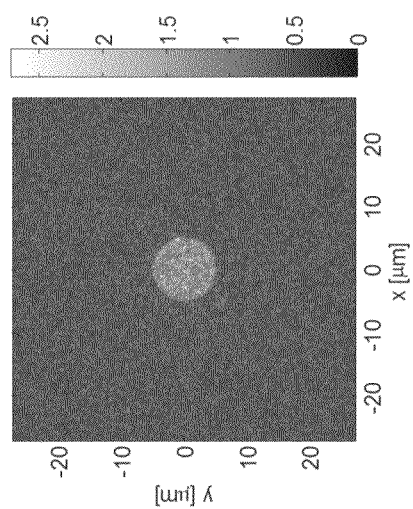

FIGS. 8A-8C show a result of reconstructed images. Here reconstructed image processing is explained in detail. In step S528, the CPU 2001 takes a sum of numerically focused amplitudes which are defocused at the same plane (z position). Then, reconstructed images are obtained as FIGS. 8A-8C. FIG. 8A and FIG. 8C clearly represent the object in FIGS. 4A and 4C, respectively. Also, FIG. 8B represents the object in FIG. 4B even if some shape is observed. Note that, although FIG. 8B can be obtained by the procedure above, FIG. 8B also can be obtained by just taking sum of the amplitudes in FIGS. 7A-7D, because the numerical focusing amount is zero.

Although FIGS. 8A-8C are more distinct than FIGS. 9A-9C, respectively, FIGS. 9A-9C may be considered representing FIGS. 4A-4C, respectively. In other words, the optical system can obtain reconstructed images based on FIG. 7A, 7B, 7C or 7D which corresponds to one certain random phase distribution of the illumination. Accordingly, it's possible to obtain a reconstructed image based on one or more complex amplitude(s) and one or more random phase distribution(s) of the illumination.

Although FIG. 3 shows the illumination distribution with a disk shape, the present embodiment is not limited to this. For example, FIGS. 10A-10B show another example of the illumination distribution with an annular shape. FIG. 10A shows amplitude distribution and FIG. 10B shows phase distribution. These distributions can be obtained by replacing the illumination aperture 1103, diffuser 1104, and aperture 1011 in FIG. 1A by an illumination aperture, and diffuser, and an aperture compatible the annular shape. Also these distributions can be obtained by replacing the CGH 1107 in FIG. 1B with a CGH compatible the annular shape. Also these distributions can be obtained by replacing the SLM 1106 in FIG. 1C with an SLM compatible the annular shape. This shape has an ability to make image of each point in the object 1009 that is bigger than points sparse in defocused planes.

FIGS. 11A-11C show reconstructed images, and amplitude distributions at each z position. These reconstructed images are calculated based on complex amplitudes acquired when illumination which has amplitude distribution and phase distribution shown FIGS. 10A and 10B are used. FIGS. 11A and 11C represent the object in FIGS. 4A and 4C, respectively, more clearly. FIG. 11B represents the object in FIG. 4B, and sparser than the embodiment above, but slightly the shape corresponding to the annular illumination shape is observed.

In addition, FIGS. 12A and 12B show one example of the illumination distribution with a bowl shape. FIG. 12A shows amplitude distribution and FIG. 12B shows phase distribution. These distributions can be obtained by replacing the illumination aperture 1103 and diffuser 1104 and aperture 1011 in FIG. 1A by an illumination aperture and diffuser and an aperture compatible with the bowl shape. Also these distributions can be obtained by replacing the CGH 1107 in FIG. 1B with a CGH compatible with the bowl shape. Also these distributions can be obtained by replacing the SLM 1106 in FIG. 1C with an SLM compatible with the bowl shape. This shape has an ability to make image of each point in the relatively large object sparse in defocused planes. As can be seen in FIG. 13B, the optical system can reproduce phase information more faithfully by using the illumination distribution shown FIGS. 12A-12B.

FIGS. 13A-13C show reconstructed images and amplitude distributions at each z position. These reconstructed images are calculated based on complex amplitudes acquired when illumination that has amplitude distribution and phase distribution shown FIGS. 12A and 12B are used. FIGS. 13A and 13C represent the object in FIGS. 4A and 4C more clearly. The clarity of the image in FIGS. 13A and 13C are more distinct than the embodiment above. FIG. 13B represents the object in FIG. 4B more clearly.

Accordingly, the information along the optical axis or tomographic images which is about amplitude object, can be obtained by post processing, without an extra time for an acquisition. The acquisition time for amplitude objects is dramatically reduced by taking complex amplitude images using a numerical focusing as a post processing, and the conventional mechanical focusing is not required.

[Measurement of Phase Object]

Figure 14:
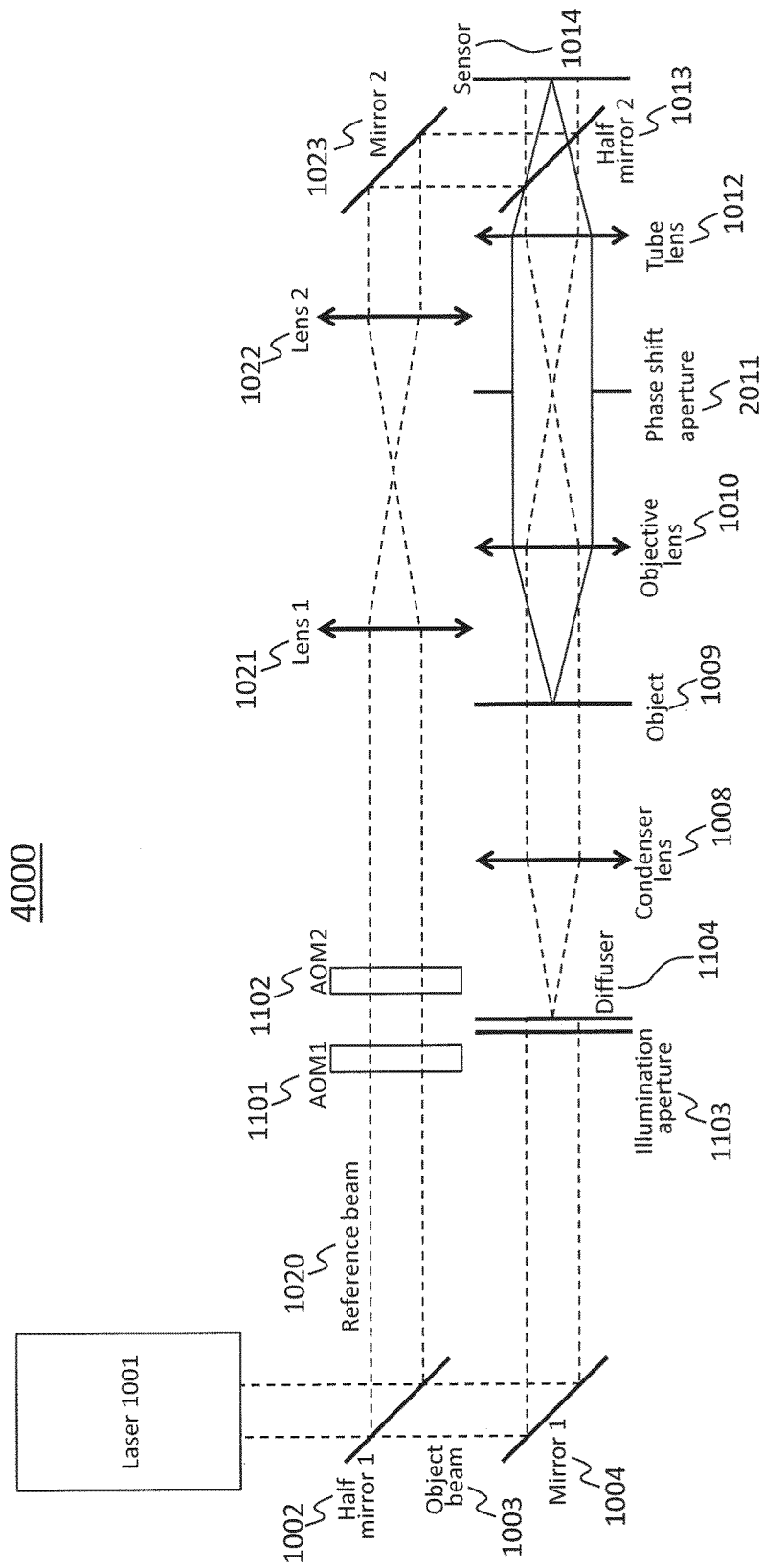
FIG. 14 illustrates an exemplary system configuration to take phase shift holograms (complex amplitude) with a mechanical phase shift aperture.

The system for the phase object will be described next. FIG. 14 shows one example of the optical system 4000 with a phase shift aperture 2011. The differences from FIG. 1A are Phase shift aperture 2011 and shape of the illumination distribution. When the system measures the phase object, the aperture 1011 of FIG. 1A is replaced with the phase shift aperture 2011 and the illumination distribution shown FIGS. 10A-10B or FIGS. 12A-12B can be applied. The phase shift aperture 2011 has the same amplitude distribution as the amplitude distribution of illumination, and the phase shift amount is zero where the amplitude is zero, and the phase shift amount is π/2 where the amplitude isn't zero. The illumination distribution shown in FIG. 3 can't be applied to the system shown in FIG. 14. Also, the system shown in FIGS. 1B and 1C can be modified in the same manner as FIG. 1A, and the modified system can be applied to system for measuring the phase object.

Figure 15A:
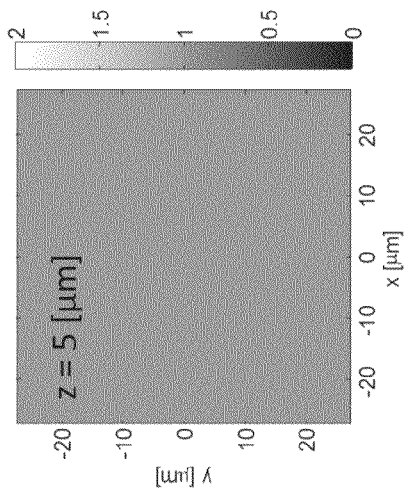
FIGS. 15A, 15C and 15E illustrate amplitude distributions at z=−5 to +5 [μm] of a phase object, respectively.
Figure 15B:
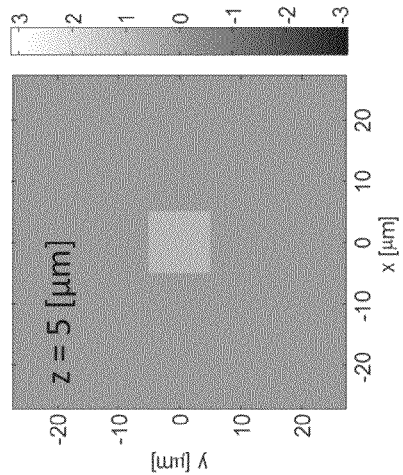
FIGS. 15B, 15D and 15F illustrate phase distributions at z=−5 to +5 [μm] of the phase object, respectively.
Figure 15C:
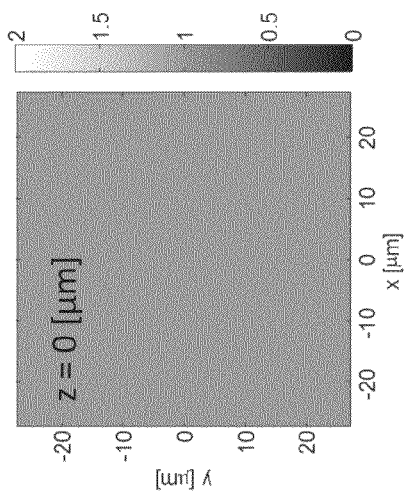
Figure 15D:
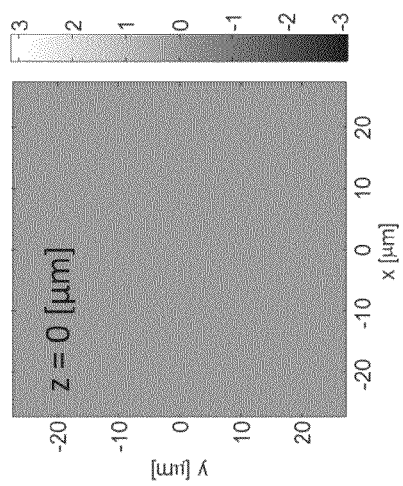
Figure 15E:
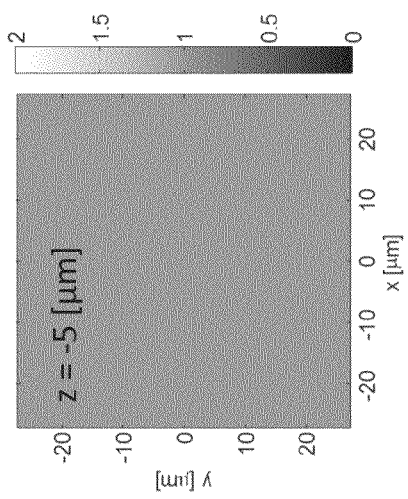
Figure 15F:
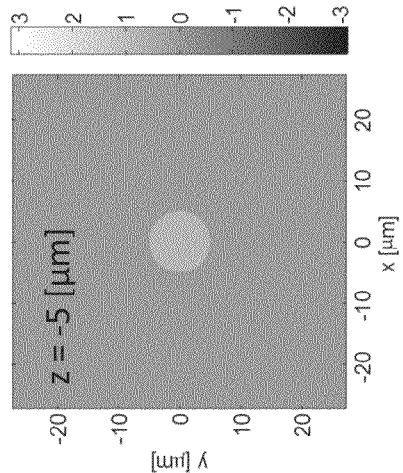

FIGS. 15A-15F show a test object, which is a phase object. FIGS. 15A and 15B show amplitude distribution and phase distributions of the test object at z=−5 [μm] respectively, FIGS. 15 C and 15D show ones at z=0 [μm] respectively, FIGS. 15E and 15F show ones at z=5 [μm] respectively. The axis z is along an optical axis. This test object can be thought as a phase object. For example, there is a disk shape refractive index difference from surroundings at z=−5 [μm], and there is a rectangle shape refractive index difference object at z=5 [μm]. A remarkable thing is that there is nothing at z=0 [μm], so the nothing, which means no shape of the disk or the rectangle, is expected as a reconstructed image there.

Figure 16A:
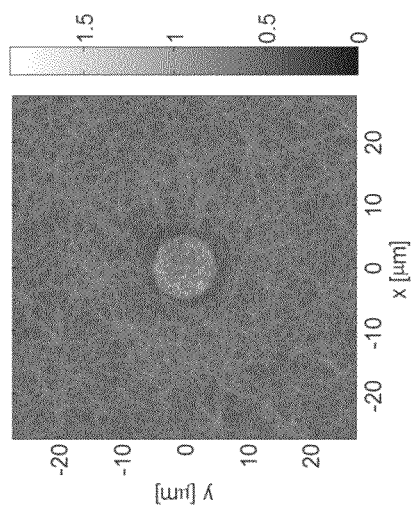
FIGS. 16A-16C illustrate exemplary reconstructed images for the Zernike phase ring illumination at z=−5 to +5 [μm].
Figure 16B:
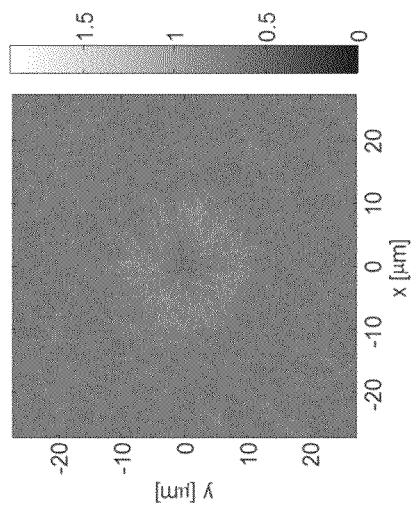
Figure 16C:
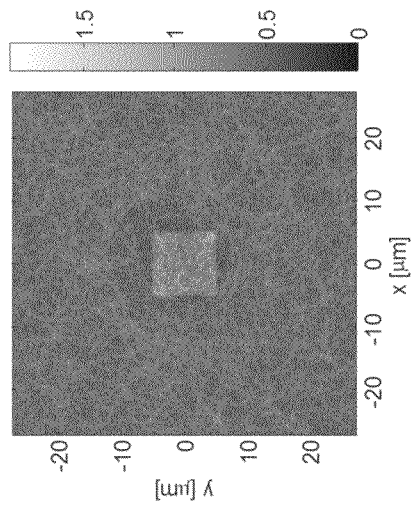

FIGS. 16A-16C shows exemplary reconstructed images, and amplitude distributions at each z position. Note that, the calculations by the CPU 2001 for numerical focusing are basically the same as those described above with reference to FIG. 5A-8C, and therefore, detailed descriptions thereof are not repeated. However, the phase information is transferred into the amplitude information by phase shifting and FIGS. 16A-16C illustrate phase information of Object 1009.

Figure 17A:
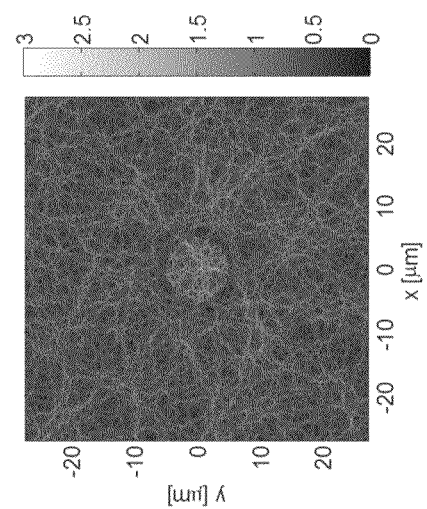
FIGS. 17A and 17B illustrate an exemplary reconstructed images for the Zernike phase ring illumination at z=−5 [μm] and at z=+5 [μm].
Figure 17B:
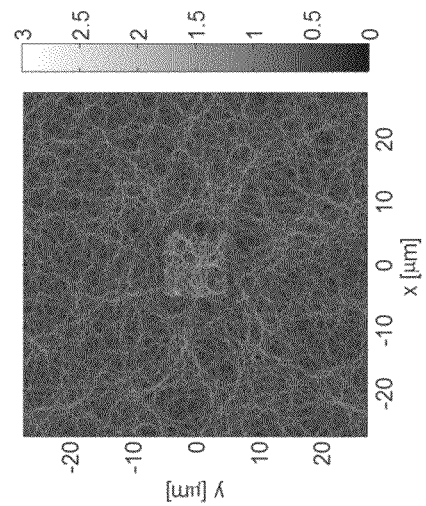

FIGS. 17A-17B show another result of reconstructed images. FIG. 17A corresponds to v(x, y, −5) and FIG. 17B corresponds to v(x, y, +5). As with the foregoing embodiments, the CPU 2001 calculates the reconstructed image, which is on the phase information, based on complex amplitude or one random phase distribution of the illumination.

In the foregoing description, the optical system 4000 includes the phase shift aperture 2011. However, the present embodiment is not limited to this. The function of the phase shift aperture can be done by software as a post processing. Here, the system which reflects a modification made to the system of FIG. 14 is applied. The modification is done by replacing the phase shift aperture 2011 illustrated in FIG. 14 with the aperture 1011 illustrated FIG. 1A. Other configurations are similar to that explained with reference to FIG. 14, and therefore, a description thereof is not repeated.

<Another Flowchart for Calculating Complex Amplitude and Numerical Focusing>

Figure 18:
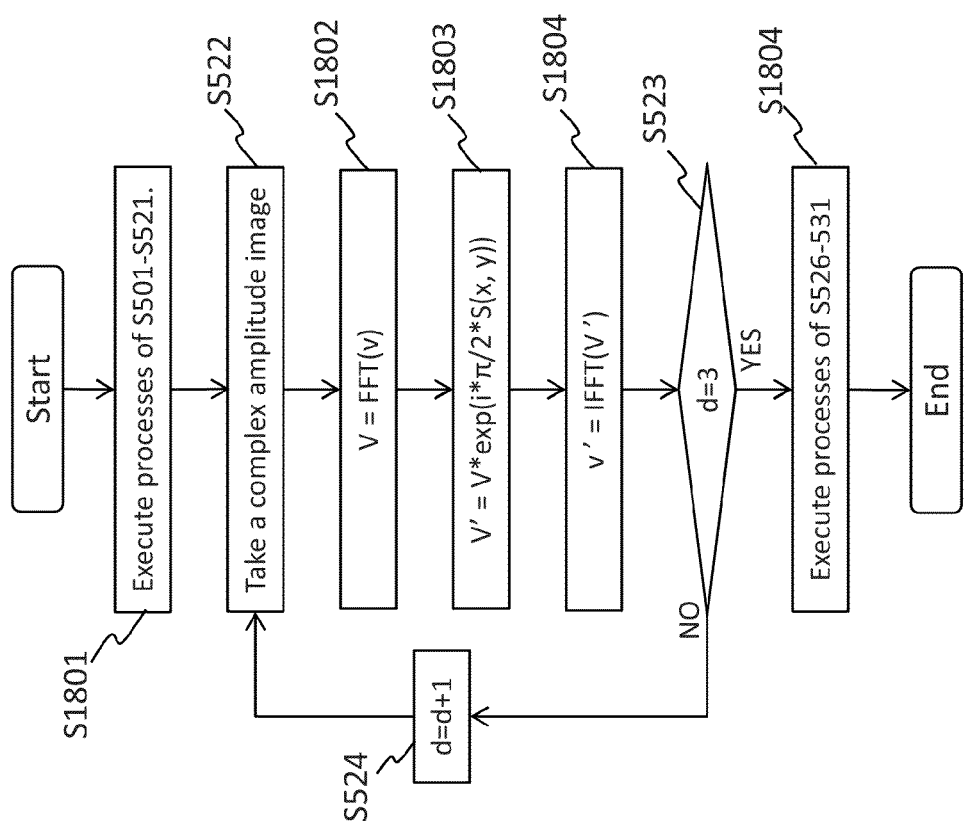
FIG. 18 is a flow chart illustrating taking tomographic images by a system without phase shift aperture.
Figure 19A:
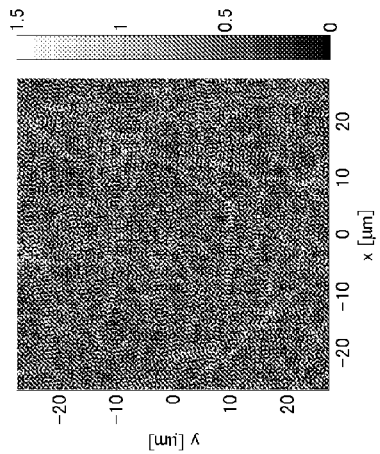
FIGS. 19A-19D illustrate exemplary phase shift holograms with π/2 phase shift, with π phase shift, with 3π/2 phase shift and with 2π phase shift, respectively.
Figure 19B:
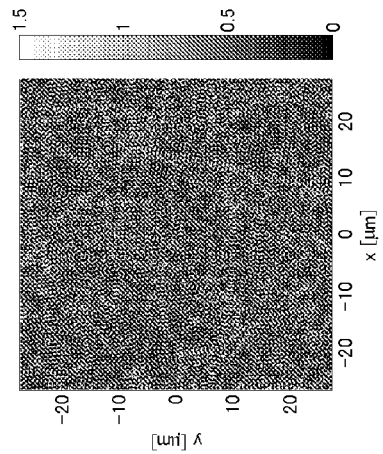
Figure 19C:
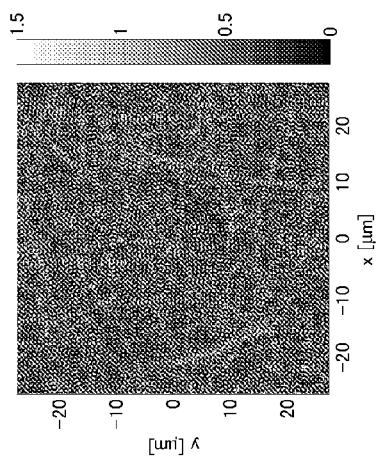
Figure 19D:
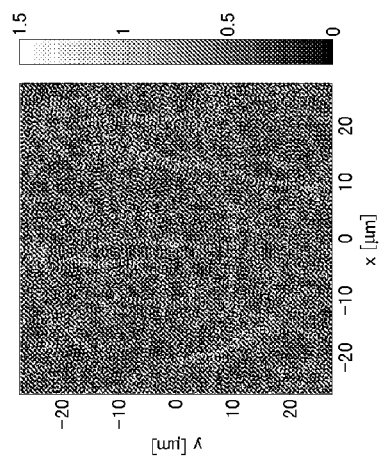
Figure 20A:
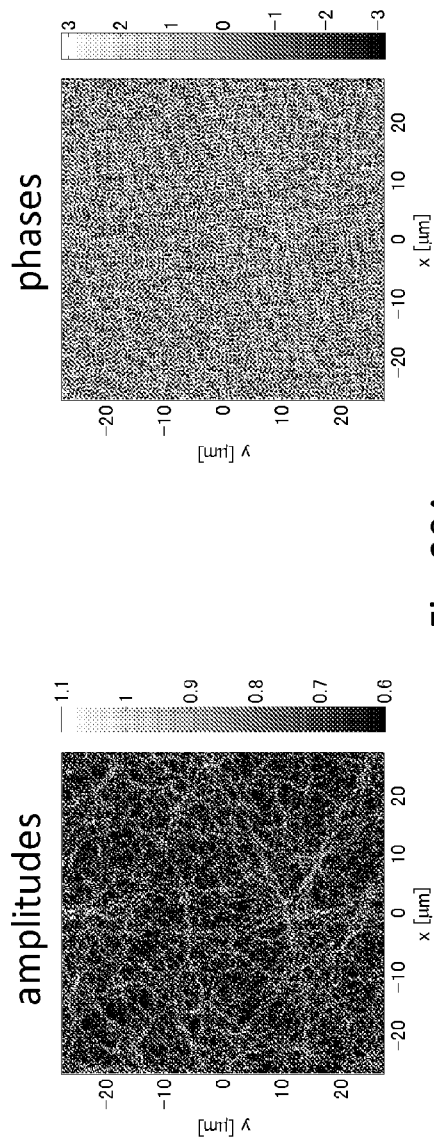
Figure 20B:
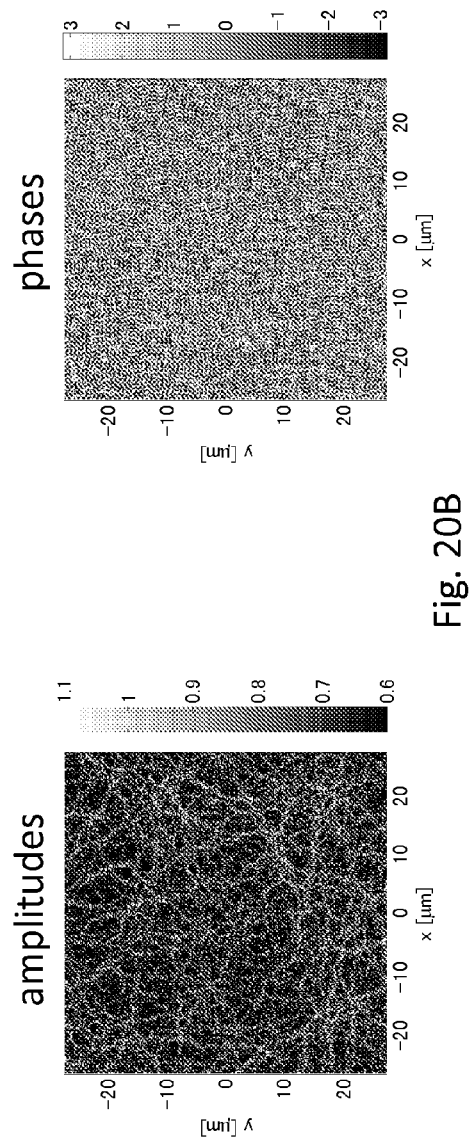
Figure 21A:
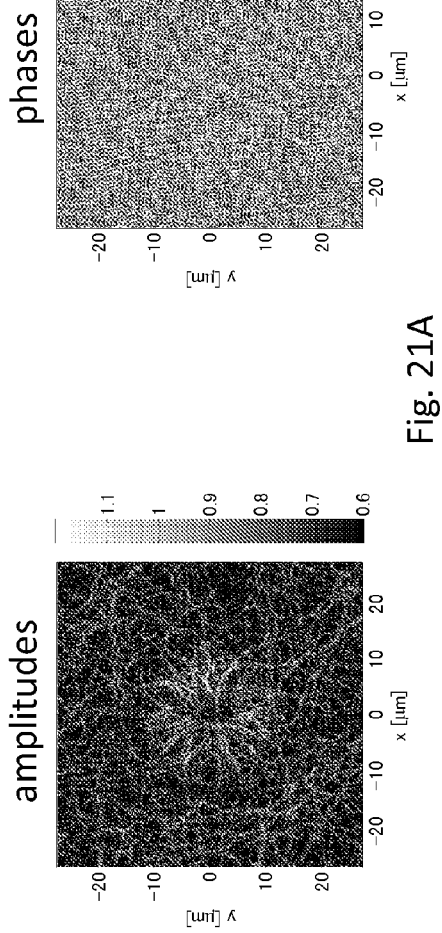
Figure 21B:
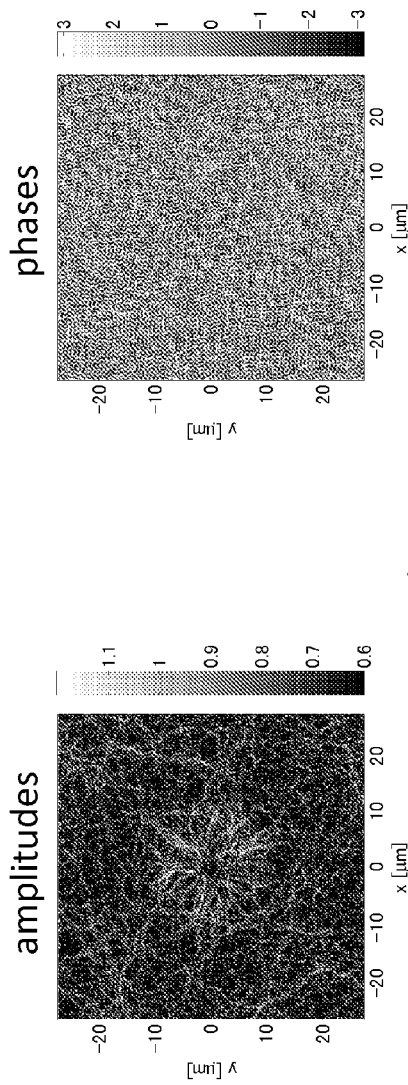

FIG. 18 shows a flowchart for calculating complex amplitude and numerical focusing with the optical system without hardware or mechanical phase shift aperture. In step S1801, the processes illustrated in step S501 through S521 of FIG. 5 are executed. FIGS. 19A-19D show phase shift holograms with four phase shifted reference beams, $\pi/2$ (FIG. 19A), $\pi$ (FIG. 19B), $3\pi/2$ (FIG. 19C) and $2\pi$ (FIG. 19D) obtained in step S 1801. In step S522, the CPU 2001 takes complex amplitudes image (calculates complex amplitudes).

FIGS. 20A-20D show exemplary complex amplitudes calculated by the CPU 2001 based on the equation (4). In step S1802, the CPU 2001 calculates the spectrum V from the complex amplitude v(x, y, 0) by FFT. The CPU 2001 reads the complex amplitude v(x, y, 0) corresponding to value of current variable "d". In step S1803, the spectrum V is multiplied by the phase shift aperture factor exp[i*π/2*S(x, y)] to obtain the new spectrum V'. S(x, y) is the illumination amplitude, e.g. FIG. 10A. In step S1804, complex amplitude v' is recalculated from the spectrum V' obtained at S1803 by IFFT, and FIGS. 21A-21D show the complex amplitude v' which takes in consideration the object light that is assumed to have gone through the phase shift aperture. According to steps S1802-S1804, the CPU 2001 reflects an influence from the object light that is assumed to go through the phase shift aperture 2011 to the complex amplitude which is calculated in step S1804.

$$V\left(\frac{\alpha}{\lambda}, \frac{\beta}{\lambda}, 0\right) = \int\int v(x, y, 0)\exp\left[-i2\pi\left(\frac{\alpha}{\lambda}x + \frac{\beta}{\lambda}y\right)\right]dxdy \quad (4)$$

$$v'(x, y, 0) = \int\int V\left(\frac{\alpha}{\lambda}, \frac{\beta}{\lambda}, 0\right)\exp\left[i\frac{\pi}{2}S(x, y)\right]\exp\left[i2\pi\left(\frac{\alpha}{\lambda}x + \frac{\beta}{\lambda}y\right)\right]d\frac{\alpha}{\lambda}d\frac{\beta}{\lambda} \quad (5)$$

With these steps from S1802 to S1804, the phase information of the image v is transferred to the amplitude of the image v'. The CPU 2001 input v' (x, y, 0) which is left side of an equation (5) into v(x, y, 0) which is in right side of an equation (5). In this way, the CPU 2001 calculates complex amplitudes, which reflects influence when the object light is assumed to have gone through the phase shift aperture 2011 on the basis of the interference of the reference beam 102 and object beam which hasn't gone through the phase shift aperture 2011.

Although in FIG. 18, calculating the numerical focusing is shown after processes of step S1802-1804, the present exemplary embodiment is not limited to this. The same result can be obtained when process order is changed, for example, the processes related to the phase shift aperture may be done after the numerical focusing (S528).

In this instance, after step S528, the CPU 2001 inputs v(x, y, 0) which is left side of an equation (6) into v(x, y, 0) which is in right side of an equation (6). Here v(x, y, 0) read by the CPU 2001 is corresponding to value of current variable "d" stored in the RAM 2002. Then the CPU 2001 calculates the v'(x, y, z) which is left side of an equation (7) by using V(α/v, β/λ, z) which is left side of an equation (6) and an equation (7). The v' (x, y, z) corresponds to complex amplitude which reflects influence when the object light is assumed to go through the phase shift aperture 2011.

$$V\left(\frac{\alpha}{\lambda}, \frac{\beta}{\lambda}, z\right) = \int\int v(x, y, z)\exp\left[-i2\pi\left(\frac{\alpha}{\lambda}x + \frac{\beta}{\lambda}y\right)\right]dxdy \quad (6)$$

$$v'(x, y, z) = \int\int V\left(\frac{\alpha}{\lambda}, \frac{\beta}{\lambda}, z\right)\exp\left[i\frac{\pi}{2}S(x, y)\right]\exp\left[i2\pi\left(\frac{\alpha}{\lambda}x + \frac{\beta}{\lambda}y\right)\right]d\frac{\alpha}{\lambda}d\frac{\beta}{\lambda} \quad (7)$$

In the foregoing description, it is explained with the illumination distribution shown FIGS. 10A-10B or FIGS. 12A-12B, but the present embodiment is not limited to this. For example, FIGS. 22A-22B show another example of the illumination distribution with a double annular shape. FIG. 22A shows another exemplary amplitude distribution and FIG. 22B shows another exemplary phase distribution. This shape has an ability to make image of each point in the object that is bigger than points sparse in the defocused planes. As shown FIG. 22B, when the diffuser 1104 works as the diffuser, the phase distribution also becomes random.

FIGS. 23A-23C show reconstructed images, and amplitude distributions at each z position. FIGS. 23A and 23C represent the object in FIGS. 15B and 15F, respectively, more clearly. FIG. 23B represents the object in FIG. 15B, and sparser than the embodiment above, but a slight shape corresponding to the annular illumination shape is observed.

FIGS. 24A-24B show another example of the illumination distribution with a double annular dot shape. FIG. 24A shows amplitude distribution and FIG. 24B shows phase distribution. This shape has an ability to make image of relatively large object sparse in the defocused planes.

FIG. 25 shows reconstructed images, and amplitude distributions at each z position. FIGS. 25A and 25C represent the object in FIGS. 15B and 15F, respectively, as well as FIGS. 23A and 23C, respectively. FIG. 25B represents the object in FIG. 15B, and sparser than the embodiment above.

Accordingly, the information along the optical axis or tomographic images which is about phase object, can be obtained by a post processing, without an extra time for an acquisition. The acquisition time for phase objects is dramatically reduced by taking complex amplitude images using a numerical focusing as a post processing, and the conventional mechanical focusing is not required.

Other Embodiments

Aspects of the present invention can also be realized by a computer of a system or apparatus (or devices such as a CPU or MPU) that reads out and executes a program recorded on a memory device to perform the function of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer, for example via a network or from a recording medium of various types serving as the memory device (e.g., computer-readable medium).

What is claimed is:

1. An apparatus for tomographic imaging of an object comprising:
   a coherent light source that generates illumination, which comprises coherent light;
   a separator configured to split the coherent light into a reference light and a illumination light;
   a shifter configured to adjustably shift a relative phase difference between the illumination light and the reference light, by shifting the phase of the reference light or the illumination light;
   a spatial phase adjuster configured to adjust the phase of the illumination light such that the illumination light has a random phase distribution in a plane perpendicular to the optical axis;
   a coupler which combines the reference light and object light, wherein the object light is light from the object which has been illuminated by the illumination light, the reference light and the object light being interfered;
   a detector configured to detect an interference caused by the reference light and the object light, wherein object light does not go through a phase shift aperture; and
   a processor configured to calculate a complex amplitude for an optical propagation which reflects influence when the object light is assumed to go through the phase shift aperture based on the detected interference.

2. The apparatus according to claim 1, wherein the spatial phase adjuster changes the illumination light as a first illumination which has a first random phase distribution to a second illumination which has a second random phase distribution, and the coupler, the shifter and the detector work for the first and second random distribution.

3. The apparatus according to claim 1, wherein the illumination light is disk shape or annular shape.

4. The apparatus according to claim 1, wherein the illumination light is a double annular shape or a double annular dot shape.

5. The apparatus according to claim 1, wherein the shifter is also the spatial phase adjuster.

6. The apparatus according to claim 1, wherein the shifter shifts the relative phase difference by changing the optical path length along the optical axis.

7. The apparatus according to claim 1, wherein the processor is configured to calculate the optical propagation based on the detected interference for the each of four phase shifts of the shifter.

8. An apparatus for tomographic imaging of an object comprising:
   a light unit configured to generate illumination, which comprises coherent light and has random phase distribution in a plane perpendicular to an optical axis, for illuminating an object;
   a coupler which combines a reference light and an object light which is from the light unit and passed through the object, the reference light and the object light being interfered;
   a shifter configured to shift relative phase difference between the object light and the reference light;
   a detector configured to detect an interference caused by the reference light and object light for the each phase, wherein object light does not go through a phase shift aperture; and
   a processor configured to calculate a complex amplitude which takes into consideration that the object light is assumed to have gone through the phase shift aperture based on the detected interference, and then to calculate a complex amplitude at a defocus position using numerical focusing.

9. An apparatus for tomographic imaging of an object comprising:
   a separator configured to split coherent light into a reference light and a illumination light;
   a shifter configured to adjustably shift a relative phase difference between the illumination light and the reference beam, by shifting the phase of the reference light or the illumination light;
   a phase adjustment unit configured to adjust the phase of the illumination light such that the illumination light has a random phase distribution in a plane perpendicular to the optical axis;
   a coupler which combines the reference light and object light, wherein the object light is light from the object which has been illuminated by the illumination light, the reference light and the object light being interfered;
   a detector configured to detect an interference caused by the reference light and the object light, wherein object light does not go through a phase shift aperture; and
   a processor configured to acquire a complex amplitude at a defocus position by calculating the detected interference using numerical focusing, and then calculate a complex amplitude which takes into consideration that the object light is assumed to have gone through the phase shift aperture based on the complex amplitude at the defocus position.

10. The apparatus according to claim 9, further comprising a light unit configured to generate illumination, which comprises the coherent light, wherein the light unit includes the phase adjustment unit.

11. The apparatus according to claim 1, wherein the imaging optical system includes an objective lens and a tube lens.

* * * * *